US006329420B1

(12) United States Patent
Uckun et al.

(10) Patent No.: US 6,329,420 B1
(45) Date of Patent: Dec. 11, 2001

(54) TUBULIN BINDING COMPOUNDS (COBRA)

(75) Inventors: Fatih M. Uckun, White Bear Lake; Shyi-Tai M. Jan, Roseville; Chen Mao, St. Paul, all of MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/569,314

(22) Filed: May 11, 2000

Related U.S. Application Data

(62) Division of application No. 09/352,649, filed on Jun. 29, 1999.
(60) Provisional application No. 60/091,001, filed on Jun. 29, 1998, provisional application No. 60/091,002, filed on Jun. 29, 1998, and provisional application No. 60/097,378, filed on Aug. 21, 1998.

(51) Int. Cl.$^7$ .......................... A61K 31/38; C07D 333/16

(52) U.S. Cl. ............................................. 514/438; 549/78

(58) Field of Search ............................... 549/78; 514/438

(56) References Cited

FOREIGN PATENT DOCUMENTS

| 05117169 | 5/1993 | (JP) . |
| WO 92/18465 | 10/1992 | (WO) . |
| WO 99/36414 | 7/1999 | (WO) . |
| WO 00/00469 | 1/2000 | (WO) . |

OTHER PUBLICATIONS

Avila, J., *Life Sci.*, 50, 327–334 (1992) "Microtubule Functions".
Bacon, D. et al., *J. Molec. Graphics*, 6(4), 219–220 (1988) "A Fast Algorithm for Rendering Space–Filling Molecule Pictures".
Böhm, H., *J. Comput. Aided.. Mol. Des.*, 6, 593–606 (1992) "LUDI: rule–based automatic design of new substituents for enzyme inhibitor leads".
Böhm, H., *J. Comput. Aided.. Mol. Des.*, 8(3), 243–256 (1994) "The development of a simple empirical scoring function to estimate the binding constant for a protein–ligand complex of known three–dimensional structure".
Carlson, D. et al., "Dimethyl Disulfide Derivatives of Long Chain Alkenes, Alkadienes, and Alkatrienes for Gas Chromatography/Mass Spectrometry", *Anal. Chem.*, vol. 61, No. 14, pp. 1564–1571 (1989).
Chen, Y. et al., "Tonkinecin, A Novel Bioactive Annonaceous Acetogenin from *Uvaria tonkinesis*", *J. Nat. Prod.*, vol. 59, No. 5, pp. 507–509 (1996).
Chen, Y. et al., "Solubilization, Partial Purification, and Affinity Labeling of the Membrane–Bound Isoprenylated Protein Endoprotease", *Biochemistry*, vol. 35, No. 10, pp. 3227–3237 (1996).

Colman–Saizarbitoria, T. et al., "Venezenin: A New Bioactive Annonaceous Acetogenin From the Bark of *Xylopia Aromatica*", *J. Nat. Prod.* vol. 58, No. 4, pp. 532–539 (Apr. 1995).
Connolly, M., *Science*, 221(4612), 709–713 (1983) "Solvent–Accessible Surface of Proteins and Nucleic Acids".
Downing, K. et al., *Curr. Opin. Cell Biol.*, 10, 16–22 (Feb. 1998) "Tubulin and microtubule structure".
Figadere, B. et al., "Synthesis of 2,33–Dihydro–4–Oxo–Murisolin: Conjugate Addition of Primary Alkyl Iodides to α,β–Unsaturated Ketones", *Tetrahedron Lett.*, vol. 33, No. 36, pp. 5189–5192 (1992).
Hyman, A. et al.,*J. Cell Sci.*, 111, (Pt 15), 2077–2083 (1998) "The role of nucleation in patterning microtubule networks".
Jiang, J. et al., *Cancer Research*, 58, 5389–5395 (1998) "3–(Iodoacetamido)–benzoylurea: A Novel Cancericidal Tubulin Ligand that Inhibits Microtubule Polymerization, Phosphorylates bcl–2, and Induces Apoptosis in Tumor Cells".
Jan, S. et al., *Tetrahedron Letters*, 40, 193–196 (1999) "Stereoselective Synthesis of a Versatile Intermediate for the Total Synthesis of Mono—and Bis–THF Containing Annonaceous Acetogenins".
Kimmel, C. et al., *Dev. Dynam.*, 203(3), 253–210 (1995) "Stages of Embryonic Development of the Zebrafish".
Kozielski, F. et al., *Curr. biol.*, 8(4), 191–198 (1998) "A model of the microtubule–kinesin complex based on electron cryomicroscopy and X–ray crystallography".
Kraulis, P., *J. Appl. Cryst.*, 24(5), 946–950 (1991) "Molscript: a program to produce both detailed and schematic plots of protein structures".
Li, K. et al., *Tetrahedron*, 39, 2063–2066 (1998) "Sterocontrolled Synthesis of the Tetrahydrofuran Unit of Annonaceous Acetogenins".
Luty, B. et al., *J. Comp. Chem.*, 16(4), 454–464 (1995) "A Molecular Mechanics / Grid Method for Evaluation of Ligand–Receptor Interactions".
Makabe et al., Heterocycles, vol. 43, No. 10, (1996).
Mao, C. et al., *Bioorganic & Medicinal Chemistry Letters*, 8, 2213–2218 (1998) "Structure–Based Design of N–[2–(Piperidinylethyl)]–N'–[2–(5–Bromopyridyl)]–Thiourea and N–[2–(1–Piperazinylethyl)]–N'–[2–(5–Bromopyridyl)]–Thiourea as Potent Non–Nucleoside Inhibitors of HIV–1 Reverse Transcriptase".
Merritt, E. et al., *Acta Cryst*, D50(6), 869–873 (1994) "Raster3D Version 2.0. A Program for Photorealistic Molecular Graphics".

(List continued on next page.)

*Primary Examiner*—Bernard Dentz
(74) *Attorney, Agent, or Firm*—Merchant & Gould P.C.

(57) ABSTRACT

Novel tubulin binding compounds having potent tubulin depolymerization activity and inhibitory activity against tubulin polymerization. The compounds are effective agents for inhibiting cellular proliferation, for example, in cancer cells. The compounds are adapted to interact favorably with a novel tubulin binding pocket, which pocket is useful for screening of anti-tubulin, anti-proliferation, and anti-cancer drugs.

10 Claims, 18 Drawing Sheets

OTHER PUBLICATIONS

Narla, R. et al., *Clin. Cancer Res.*, 4, 2463–2471 (1998) "Inhibition of Human Glioblastoma Cell Adhesion and Invasion by 4-(4'-Hydroxylphenyl)-amino-6, 7-dimethoxyquinazoline (WHI-P131) and 4-(3'-Bromo-4'-hydroxylphenyl)-amino-6, 7-dimethoxyquinazoline (WHI-P154)".

Nogales, E. et al., *Nature*, 391, 199–202 (1998) "Structure of the αβtubulin dimer by electron crystallography".

Schulz, S., "New Lipids From Spiders and Insects", *Chemical Abstract*, vol. 124, No. 19, 1 pg. (May 6, 1996).

Schulz, S. et al., "2,5-Dialkyltetrahydrofurans, Common Components of the Cuticular Lipids of Lepidoptera", *Z. Naturforsch*, pp. 107–116 (1998).

Towne, T. et al., "syn-Oxidative Polycyclizations of Hydroxypolyenes: Highly Stereoselective and Potentially Biomimetic Syntheses of all–trans–Polytetrahydrofurans", *J. Am. Chem. Soc.*, vol. 119, No. 26, pp. 6022–6028 (1997).

Uckun, F. et al., *Blood*, 85(10), 2817–2828 (1995) "In Vitro and In Vivo Activity of Topotecan Against Human B–Lineage Acute Lymphoblastic Leukemia Cells".

Vassilev, A., et al., *J. Biol. Chem.*, 274(3), 1646–1656 (1999) "Bruton's Tyrosine Kinase as an Inhibitor of the Fas/CD95 Death–inducing Signaling Complex".

Vig. R. et al., *Bioorganic & Medicinal Chemistry*, 6, 1789–1797 (1998) "Rational Design and Synthesis of Phenethyl–5–bromopyridyl Thiourea Derivatives as Potent Non–nucleoside Inhibitors of HIV Reverse Transcriptase".

Vig, R. et al., *Bioorg. & Med. Chem. Lett.*, 8, 1461–1466 (1998) "5–Alkyl–2[(Methylthiomethyl)Thio]–6–(Benzyl)–Pyrimidin–4–(1H)–Ones as Potent Non–Nucleoside Reverse Transcriptase Inhibitors of S–Dabo Series".

Woo, M. et., "Asimilobin and CIS—and Trans–Murisolinones, Novel Bioactive Annonaceous Acetogenins From The Seeds Of *Asimina Triloba*", *J. Nat. Prod.*, vol. 58, No. 10, pp. 1533–1542 (Oct. 1995).

Wu, F. et al., "Additional Bioactive Acetogenins, Annomutacin And (2,4–Trans and CIS)–10R–Annonacin–A–Ones, From The Leaves of *Annona Muricata*", *J. Nat. Prod.*, vol. 58, No. 9, pp. 1430–1437 (Sep. 1995).

Ye, Q. et al., "Longicin and Goniothalamicinone: Novel Bioactive Monotetrahydrofuran Acetogenins from *Asimina Longifolia*", *J. Nat. Prod.*, vol. 58, No. 9, pp. 1398–1406 (Sep. 1995).

Makabe et al, Heterocycles, vol. 43, No. 10, 1996.*

* cited by examiner

Figure 6 A
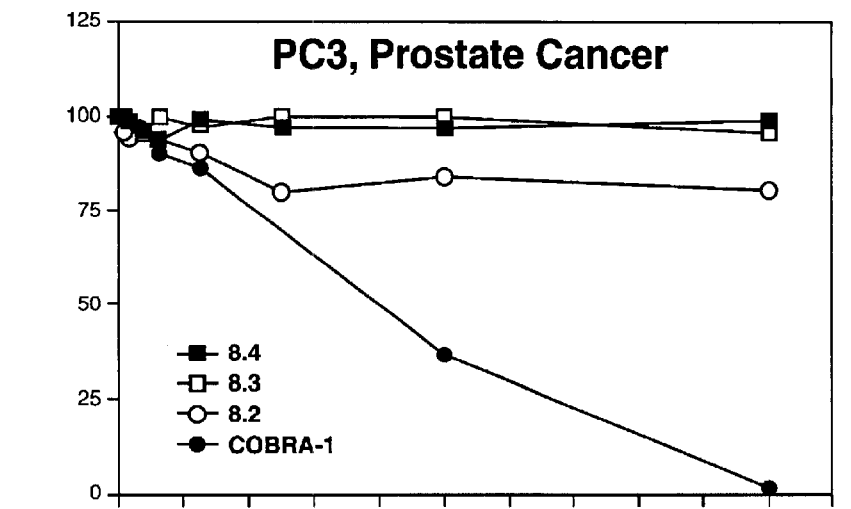
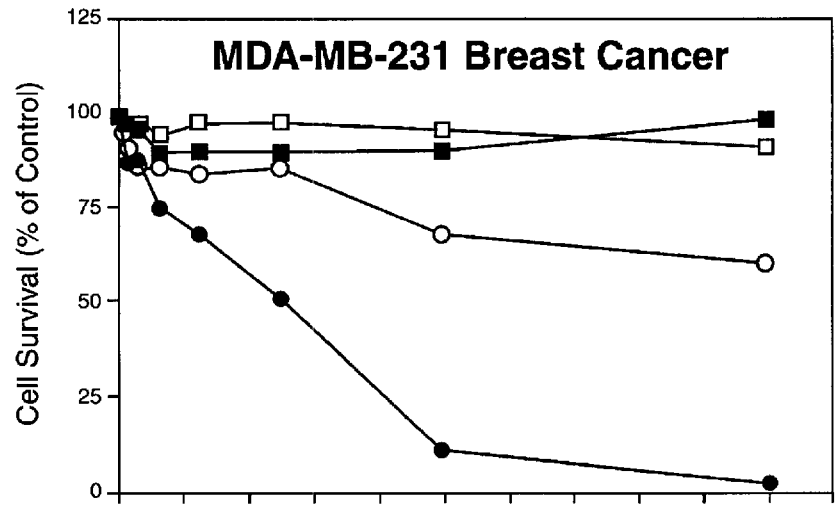
Figure 6 B
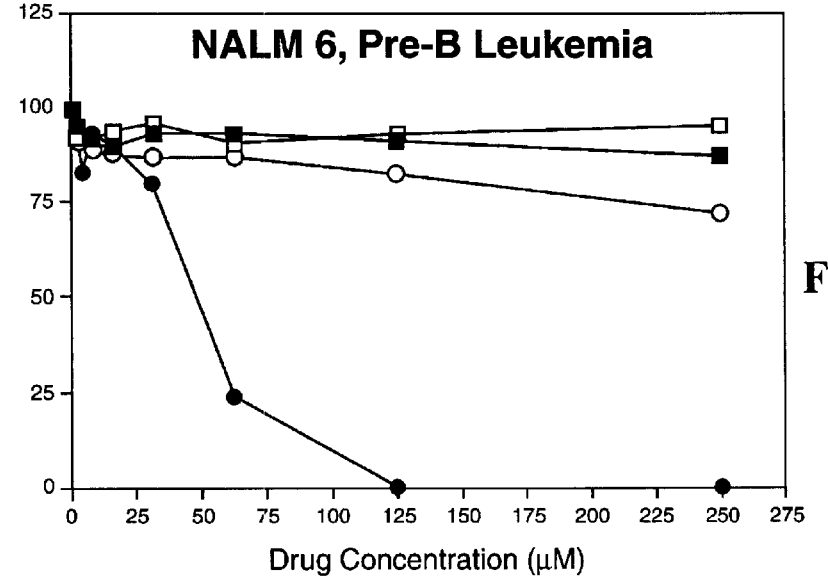
Figure 6 C

TUBULIN BINDING COMPOUNDS (COBRA)

This application is a divisional of U.S. application Ser. No. 09/352,649, filed Jun. 29, 1999 which claims benefit of Provisional Applications Ser. No. 60/091,001 filed Jun. 29, 1998, Ser. No. 60/091,002 filed Jun. 29, 1999, and Ser. No. 60/097,378 filed on Aug. 21, 1998.

FIELD OF THE INVENTION

The invention relates to a novel binding pocket of tubulin, and to novel compounds tubulin-binding compounds designed and configured to fit and interact favorably with residues of the novel binding pocket. These tubulin-binding compounds are potent inhibitors of tubulin polymerization and active anti-cancer agents.

BACKGROUND OF THE INVENTION

Cancer is a major disease that continues as one of the leading causes of death at any age. In the United States alone, it is anticipated that more than a half a million Americans will die of cancer in 1999. Currently, radiotherapy and chemotherapy are two important methods used in the treatment of cancer.

Considerable efforts are underway to develop new chemotherapeutic agents for more potent and specific anti-cancer therapy, presenting effective and efficient cytotoxicity against tumor cells, with minimal interference with normal cell function. Accordingly, there is an urgent need for the development and analysis of novel, effective anti-cancer agents.

Cellular proliferation, for example, in cancer, occurs as a result of cell division, or mitosis. Microtubules play a pivotal role in mitotic spindle assembly and cell division[1–5]. These cytoskeletal elements are formed by the self-association of the αβ tubulin heterodimers[1–5].

Recently, the structure of the αβ tubulin dimer was resolved by electron crystallography of zinc-induced tubulin sheets[6]. According to the reported atomic model, each 46×40×65 Å tubulin monomer is made up of a 205 amino acid N-terminal GTP/GDP binding domain with a Rossman fold topology typical for nucleotide-binding proteins, a 180 amino acid intermediate domain comprised of a mixed β sheet and five helices which contain the taxol binding site, and a predominantly helical C-terminal domain implicated in binding of microtubule-associated protein (MAP) and motor proteins[2, 5].

Novel tubulin-binding molecules which, upon binding to tubulin, interfere with tubulin polymerization, can provide novel agents for the treatment of cancer.

SUMMARY OF THE INVENTION

A novel binding pocket has been identified in tubulin, which binding pocket accepts and binds novel, small molecule tubulin binding compounds of the invention. Binding of the compounds of the invention to tubulin causes tubulin depolymerization and/or inhibits tubulin polymerization. The tubulin binding compounds of the invention are therapeutically effective to inhibit cellular proliferation, for example, as effective anti-cancer agents.

The first embodiment of the invention are the compounds represented by the general formula I:

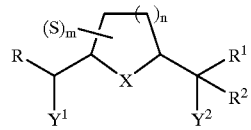

where

X is O, S, C, or $NR^aR^b$;

R is a saturated or unsaturated ($C_7$–$C_{15}$) hydrocarbon chain;

$R^1$ and $R^2$ are independently H, ($C_1$–$C_6$)alkyl, ($C_1$–$C_6$) alkenyl, $C_1$–$C_6$)alkynyl, ($C_3$–$C_7$)cycloalkyl, aryl, or heteroaryl, and may be substituted or unsubstituted;

$Y^1$ and $Y^2$ are independently H, OH, SH, CN, halogen, acyl, ($C_1$–$C_6$) alkoxy, thioacyl, ($C_1$–$C_6$)alkylthio, or $NR^aR^b$, provided that $Y^1$ and $Y^2$ are not both hydrogen;

n is 1 to 3;

m is 0 to 10; and each S is independently OH, SH, $CO_2H$, halogen, CN, acyl, thioacyl, ester, thioester, alkoxy, aryloxy, alkylthio, arylthio, alkyl, alkenyl, alkynyl, ($C_3$–$C_7$) cycloalkyl, aryl, heteroaryl, C(=O)$NR^aR^b$, or $NR^aR^b$, which may be substituted or unsubstituted. Taken together, two of S can form a ring, or any two adjacent S can form a double bond between two carbons to which they are attached. Any two adjacent carbons can form a double bond.

$R^a$ and $R^b$ are each independently hydrogen, acyl, alkyl, ($C_3$–$C_7$)cycloalkyl, aryl, or heteroaryl; or $R^a$ and $R^b$ together with the nitrogen to which they are attached form a ring such as pyrrolidino, piperidino, morpholino, or thiomorpholino.

Preferred compounds of formula I are shown in the structures below:

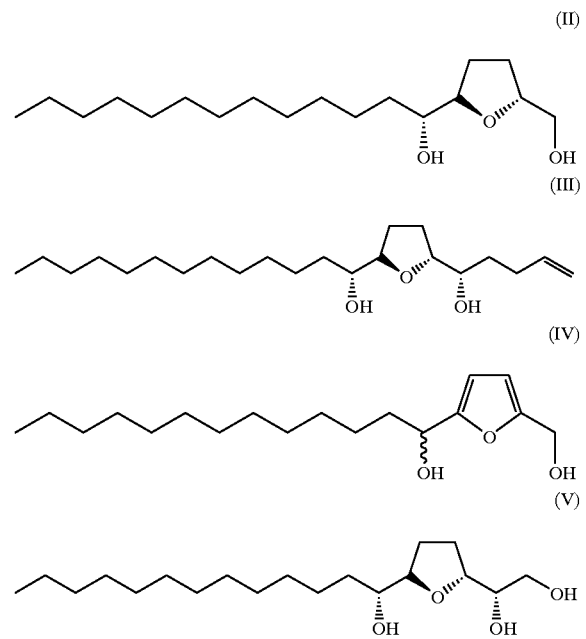

The second embodiment of the invention are the compounds represented by the general formula VI:

where
- R is a saturated or unsaturated ($C_7$–$C_{15}$) hydrocarbon chain;
- Y is H, OH, SH, CN, halogen, acyl, ($C_1$–$C_6$)alkoxy, thioacyl, ($C_1$–$C_6$)alkylthio, or $NR^aR^b$; where $R^a$ and $R^b$ are each independently wherein $R^a$ and $R^b$ are each independently hydrogen, acyl, ($C_1$–$C_6$)alkyl, ($C_3$–$C_7$) cycloalkyl, aryl, or heteroaryl; or $R^a$ and $R^b$ together with the nitrogen to which they are attached form a ring such as pyrrolidino, piperidino, morpholino, or thiomorpholino;
- D is a ($C_5$–$C_{12}$) hydrocarbon comprising at least one heteroatom, and having at least one polar group; and
- X comprises C, S, N, P, or O.

A Preferred compounds of formula VI is shown in the structure below:

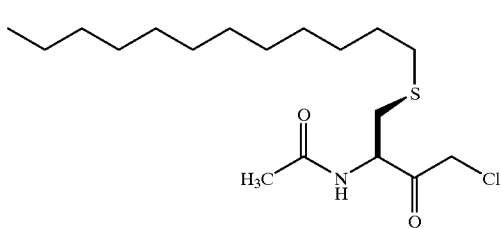

(VII)

Specific compounds, compositions, and methods for use of the binding pocket and compounds of the invention are shown more fully in the detailed description below.

BRIEF DESCRIPTION OF THE FIGURES

FIGS. 6A–6C are graphs showing cell survival curves for human cancer cells treated with COBRA-1 and compounds 8.2, 8.3, and 8.4.

DETAILED DESCRIPTION OF THE INVENTION

Definitions

Figure 1A:
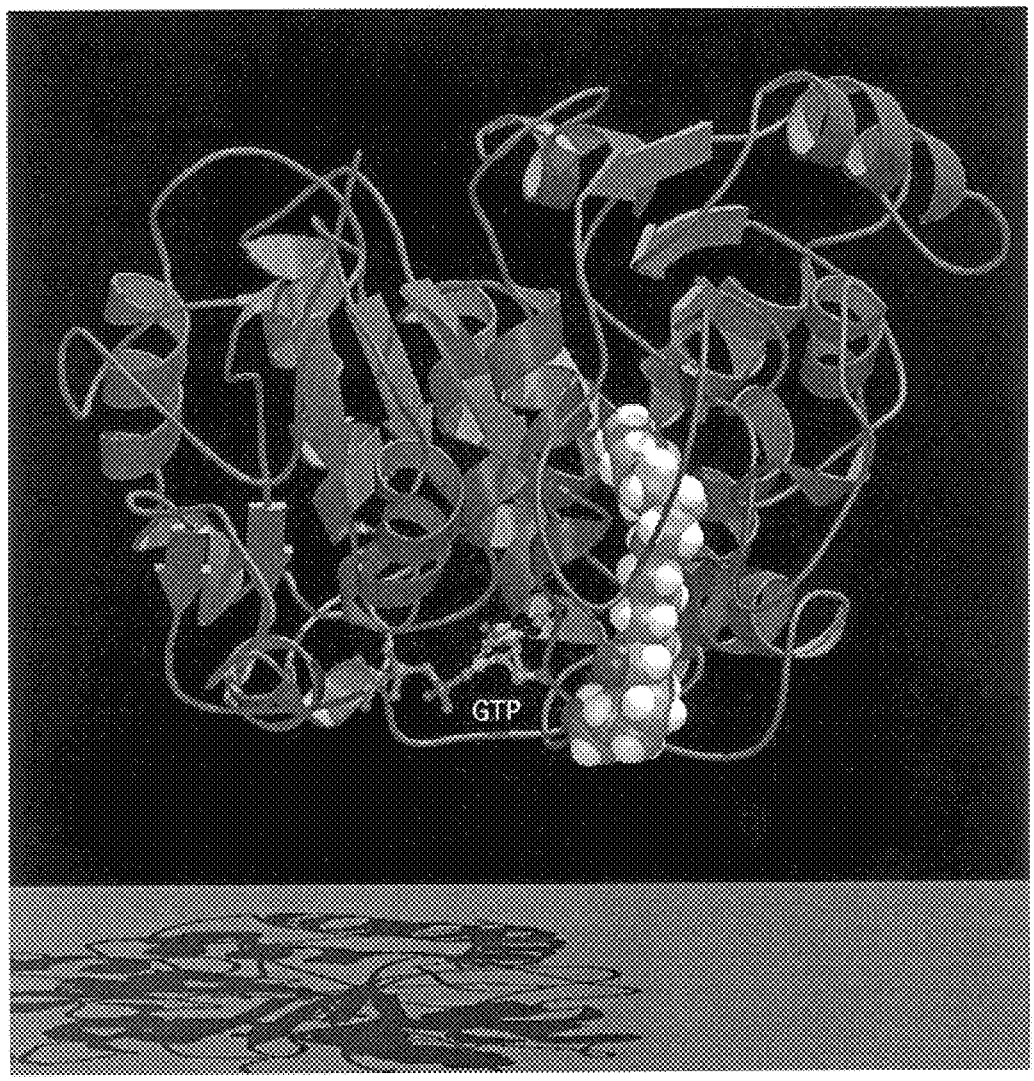
FIG. 1A is a ribbon representation of the α tubulin structure and a space-filling model of the compound COBRA-1 docked into the taxol binding mirror site on α tubulin.

All scientific and technical terms used in this application have meanings commonly used in the art unless otherwise specified. As used in this application, the following words or phrases have the meanings specified.

As used herein, "acyl" comprises a carbon attached to oxygen by a double bond.

As used herein, "alkyl", includes both branched and straight-chain saturated aliphatic hydrocarbon groups having the specified number of carbon atoms. As a preferred embodiment, chains of 1 to 22 carbon atoms are included.

As used herein, "alkythio" comprises a sulfur attached to an alkyl by a single bond.

As used herein, "alkene" and "alkenyl", includes both branched and straight chain aliphatic hydrocarbon groups that have at least one double bond.

As used herein, "alkoxy", includes saturated and unsaturated, branched and straight chain aliphatic hydrocarbon groups having a specified number of carbon atoms where at least one carbon atom forms a single-bond to an oxygen atom.

As used herein, "alkene" and "alkynyl" includes both branched and straight chain aliphatic hydrocarbon groups that have at least one triple bond.

As used herein "amine", includes primary, secondary, and tertiary amines.

As used herein, "aryl" includes aromatic hydrocarbon compounds.

As used herein, "aryloxy" comprises an oxygen attached to an aryl by a single bond.

As used herein, "cycloalkyl" includes cyclic alkanes.

As used herein, an "ester" comprises a carbon attached to a first oxygen by a double bond and to a second oxygen by a single bond.

As used herein "halogen" or "halo" substituent includes fluoro, chloro, bromo, and iodo.

As used herein, "heteroaryl" includes aromatic hydrocarbon compounds having at least one atom of O, N or S in an aromatic ring.

As used herein, "pharmaceutically acceptable salt thereof" includes an acid addition salt or a base salt.

As used herein, "pharmaceutically acceptable carrier" includes any material which, when combined with a compound of the invention, allows the compound to retain biological activity, such as the ability to induce apoptosis of leukemia or breast tumor cells, and is non-reactive with the subject's immune system. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.).

"Substituted cycloalkyl" includes cyclic hydrocarbons having substituents including halo, alkyl, alkenyl, oxyalkyl, oxyalkenyl, haloalkyl, haloalkenyl, and aryl.

"Substituted cycloalkenyl" includes cyclic hydrocarbons having at least one double bond where substituents include halo, alkyl, alkenyl, oxyalkyl, oxyalkenyl, haloalkyl, haloalkenyl, and aryl.

"Substituted aryl" includes aromatic hydrocarbons having substituents including hydroxyl, amino, aminomethyl, halo, alkyl, alkenyl, oxyalkyl, oxyalkenyl, haloalkyl, haloalkenyl, and aryl.

"Treating" or "Treatment" in the context of this invention means the prevention or reduction in severity of symptoms or effects of a pathological condition, including prolonging life expectancy. In the context of cancer therapy, treatment includes prevention of tumor growth, reduction of tumor size, enhanced tumor cell death, and increased apoptosis.

COBRA Binding Pocket on Tubulin

The COBRA binding pocket of tubulin is a previously-unidentified region within the intermediate domain of tubulin, located between the GDP/GTP binding site and the taxol binding site, and having the approximate dimensions 6 Å×22 Å×7 Å. The pocket of the invention has an abundance of leucine residues (7 leucine and 2 isoleucine) providing a highly hydrophobic binding environment. It is characterized by a narrow cavity with elongated dimensions, suitable for accomodating aliphatic chain of up to about 12 carbons (see FIGS. 1A–1B).

The residues lining the narrow elongate cavity and suitable for interraction with the tail piece of COBRA compounds include Asp367, Leu217, Val275, Ile 276, Leu368, Tyr272, Ile212, Ile234, Gln233, Leu230, His229, Ile209, Ile231, and Leu23. Residues of the pocket suitable for interaction with the head piece of COBRA compounds include Asn226, Pro222, and Ile219. (See FIG. 1B)

COBRA synthetic designs adapted to permit favorable interactions with potential binding residues in the COBRA binding pocket of tubulin include those providing polar groups in the head piece and hydrophobic groups along the aliphatic tail piece to induce favorable interactions with the pocket, and thereby increase attraction of the molecule to the pocket as well as residence time of the molecule in the binding pocket.

Compounds of the Invention

In general, the compounds of the invention include an aliphatic tail piece substituted with hydrophobic moieties (R) and a non-linear polar head piece. A general formula showing one embodiment of COBRA compounds suitable for binding to the COBRA binding pocket of tubulin is formula I:

where
X is O, S, C, or $NR^aR^b$;
R is a saturated or unsaturated ($C_7$–$C_{15}$) hydrocarbon chain;
$R^1$ and $R^2$ are independently H, ($C_1$–$C_6$)alkyl, ($C_1$–$C_6$) alkenyl, $C_1$–$C_6$)alkynyl, ($C_3$–$C_7$)cycloalkyl, aryl, or heteroaryl, and may be substituted or unsubstituted;
$Y^1$ and $Y^2$ are independently H, OH, SH, CN, halogen, acyl, ($C_1$–$C_6$) alkoxy, thioacyl, ($C_1$–$C_6$)alkylthio, or $NR^aR^b$, provided that $Y^1$ and $Y^2$ are not both hydrogen;
n is 1 to 3;
m is 0 to 10; and
each S is independently OH, SH, $CO_2H$, halogen, CN, acyl, thioacyl, ester, thioester, alkoxy, aryloxy, alkylthio, arylthio, alkyl, alkenyl, alkynyl, ($C_3$–$C_7$) cycloalkyl, aryl, heteroaryl, C(=O)$NR^aR^b$, or $NR^aR^b$, which S may be substituted or unsubstituted. Taken together, two of S can form a ring, or any two adjacent carbons can form a double bond;
$R^a$ and $R^b$ are each independently hydrogen, acyl, alkyl ($C_3$–$C_7$)cycloalkyl, aryl, or heteroaryl; or $R^a$ and $R^b$ together with the nitrogen to which they are attached form a ring such as pyrrolidino, piperidino, morpholino, or thiomorpholino; or
a pharmaceutically acceptable acid addition salt thereof.

Preferred compounds of formula I are shown in the structures below:

In a second embodiment, the compounds of the invention comprise the following formula VI:

where R represents the elongated hydrocarbon tail piece; D represents the head piece, which is generally a non-liner hydrocarbon of about 5 to 18 carbon atoms, preferably containing at least one heteroatom and most preferably containing at least one polar functional groups. Y can be a substituted moiety such as H, OH, SH, halogen, alkyl and the like, preferably providing more polar groups and/or functional groups designed to favorably interact with the COBRA binding pocket. X is a bridging group designed to provide appropriate spacing between the head and tail pieces, and comprises C, O, N, S, or combinations thereof.

More particularly:

R is a saturated or unsaturated ($C_7$–$C_{15}$) hydrocarbon chain;

Y is H, OH, SH, CN, halogen, acyl, ($C_1$–$C_6$)alkoxy, thioacyl, ($C_1$–$C_6$)alkylthio, or $NR^aR^b$; where $R^a$ and $R^b$ are each independently wherein $R^a$ and $R^b$ are each independently hydrogen, acyl, ($C_1$–$C_6$)alkyl, ($C_3$–$C_7$)cycloalkyl, aryl, or heteroaryl; or $R^a$ and $R^b$ together with the nitrogen to which they are attached form a ring such as pyrrolidino, piperidino, morpholino, or thiomorpholino;

D is a ($C_5$–$C_{12}$) hydrocarbon comprising at least one heteroatom, and having at least one polar group; and X comprises C, S, N, P, or O.

A preferred compounds of formula VI is shown in the structure below:

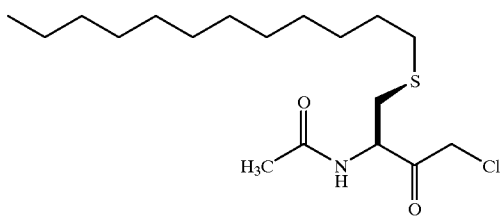

(VII)

The compounds of the invention bind to the novel COBRA binding pocket of tubulin, have an anti-tubulin effect by inhibiting tubulin assembly (polymerization) and/or by inducing depolymerization of tubulin. The tubulin binding compounds of the invention are useful as novel anti-cancer agents.

Salts

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Examples of suitable amines are N,N'-dibenzylethylenediamine, chloroprocaine, choline, diethanolamine, ethylenediamene, N-methylglucamine, and procaine.

Pharmaceutically acceptable acid addition salts are formed with organic and inorganic acids. Examples of suitable acids for salt formation are hydrochloric, sulfuric, phosphoric, acetic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for the purposes of the invention.

Depolymerization of Tubulin

The compounds of the invention bind to tubulin at a unique, novel binding pocket of tubulin. On binding of the tubulin binding compounds, tubulin is caused to depolymerize and/or inhibition of tubulin assembly results. Suitable assays for the anti-tubulin acitivity of the inventive compounds are disclosed in the Examples below.

Treatment of Proliferative Disorders

The compounds of the invention are useful to inhibit cell division and proliferation of non-cancerous cells. According to the method of the inveniton, disorders associated with cell proliferation are treated by administration of the compounds and compositions of the invention.

Such disorders include, for example, EBV-induced lymphoproliferative disease and lymphoma; neointimal hypoplasia, for example in patients with athierosclerosis and patients undergoing baloon angioplasty; proliferative effects secondary to diabetes, including vascular proliferation and retinopathy; psoriasis; benign tumors, including angiomas, fiberomas, and myomas, histiocytosis, osteoporosis, mastocytosis, and myeleoproliferative disorders such as polycytemiavera.

Tumor Treatment

The compounds of the invention can be used in methods of tumor treatment, for example, administering to a subject a compound of the invention in order to achieve an inhibition of tumor cell tubulin assembly and/or depolymerization of tumor cell tubulin, inhibition of tumor cell growth, a killing of tumor cells, induced apoptosis, and/or increased patient survival time.

The anti-cancer tubulin binding compounds of the invention are suitable for use in mammals. As used herein, "mammals" means any class of higher vertebrates that nourish their young with milk secreted by mammary glands, including, for example, humans, rabbits, and monkeys.

Administration Methods

The compounds of the present invention can be formulated as pharmaceutical compositions and administered to a mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

The compounds can be administered by known techniques, such as orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes.

More preferably, the compounds of the present invention are administered parenterally, i.e., intravenously or intraperitoneally, by infusion or injection. In one embodiment of the invention, the compounds may be administered directly to a tumor by tumor injection; or by systemic delivery by intravenous injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on the tumor cells to be treated. For example, antigens present on B-lineage cancer cells, such as CD19, can be targeted with anti-CD19 antibodies such as B43. Antibody fragments, including single chain fragments, can also be used. IL4 can also be used to target B-cells. Cancer cells expressing EGF or IGF receptors can be targeted with the binding ligand. Other such ligand-receptor binding pairs are known in the scientific literature for specific cancers. Methods for producing conjugates of the compounds of the invention and the targeting moieties are known.

Useful Dose

When used in vivo to kill or inhibit the growth of tumor cells, the administered dose is that effective to have the desired effect, such as sufficient to reduce or eliminate tumors. Appropriate amounts can be determined by those skilled in the art, extrapolating using known methods and relationships, from the in vitro data provided in the Examples.

In general, the dose of the novel tubulin binding compounds effective to achieve tumor cell apoptosis, reduction in tumors, and increased survival time, is 1–100 mg/kg body weight/dose for a direct targeted administration. The effective dose to be administered will vary with conditions specific to each patient. In general, factors such as the disease burden, tumor location (exposed or remote), host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100 mg/kg body weight is expected to be effective, although more or less may be useful.

In addition, the compositions of the invention may be administered in combination with other anti-tumor therapies. In such combination therapy, the administered dose of the tubulin binding compounds may be less than for single drug therapy.

EXAMPLES

The invention may be further clarified by reference to the following Examples, which serve to exemplify some of the embodiments, and not to limit the invention in any way.
Chemistry Methods All chemicals were purchased from Aldrich (Milwaukee, Wis.) and were used without further purification. Unless otherwise noted, each reaction vessel was secured with a rubber septa, and the reaction was performed under nitrogen atmosphere. $^1$H and $^{13}$C NMR spectra were obtained on a Varian Mercury 300 instrument at ambient temperature in the solvent specified. Melting points were determined using a Fisher-Johns melting point apparatus and are uncorrected. FT-IR spectra were recorded on a Nicolet Protege 460 spectrometer. GC/MS was obtained on a HP 6890 GC System equipped with a HP 5973 Mass Selective Detecter.

Example 1
Discovery of a Novel Target Binding Pocket on Tubulin by Molecular Modeling Studies In a systematic search for novel drug binding pockets within the intermediate domain of tubulin, we discovered a previously unidentified region with a remarkable abundance of leucine residues (viz., 7 leucine and 2 isoleucine residues) which could provide a highly hydrophobic binding environment for small molecule organic compounds. Notably, this unique region, which is located between the GDP/GTP binding site and the taxol binding site, contains a narrow cavity with elongated dimensions which could accomodate a fully stretched aliphatic chain with a length of up to twelve carbon atoms (FIG. 1). The enclosure of this putative binding cavity in alpha tubulin (but not beta tubulin) is provided in part by an eight amino acid insertion loop (residues 361–368).

Using this model, a comprehensive structure search of the organic compound files in the Hughes Institute Drug Discovery Program lead to the identification of the recently reported chiral THF-epoxides[7,8] as potential molecular templates for the rational synthesis of novel anti-cancer drugs containing structural elements capable of hydrophobic binding interactions with this leucine-rich binding cavity of tubulin.
Modeling Studies Our modeling procedure included locating a putative drug binding site via cavity searching, binding environment analysis using graphics programs including GRASP and INSIGHTII and a docking procedure based on the coordinates of tubulin. The calculation of binding constant was done according to a modified score function (LUDI score function). Fixed docking in the Affinity program within INSIGHTII[20] was used to dock the designed compounds to the unique binding pocket of tubulin which was taken from the electron crystal structure and further defined by visual inspection. We studied the region around the taxol binding mirror site on α tubulin, the latter of which has additional 8 amino acid insertion and a more closed conformation which prevents taxol binding. The docking program has the ability to define a radius of target binding region residues within a 7 Å distance from a ligand molecule. As the modeling calculations progressed, the residues within the defined radius were allowed to move in accordance with energy minimization. Ten final target positions were defined for each molecule which had starting positions randomly assigned. The final docked position of each molecule was chosen based on both the lowest energy estimation and the highest interaction score rank which was defined by a modified LUDI function (described below) for the search target. Calculations were carried out on a SGI INIDIGO2 using the CVFF force field in the Discover program and a Monte Carlo search strategy in Affinity[21]. No solvation procedures were used. Since the total number of movable atoms exceeded 200, conjugated gradient minimization was used instead of the Newton minimization method to conserve CPU time. The initial coordinates of the compounds were generated using the Sketcher module within INSIGHTII.

We imposed several modifications during the calculation of inhibitory constants ($K_i$ values) of the positioned compounds using the LUDI score function[22,23] which was previously used to successfully predict the trend of the experimental data for nonnucleoside inhibitors of the human immunodeficiency virus (HIV)-1 reverse transcriptase[24–26]. First, the molecular surface areas (MS) were directly calculated from the coordinates of the compounds in docked conformations using the MS program[9]. Next, we re-evaluated the number of rotatable bonds (NR) which are sometimes inaccurately assessed by INSIGHTII. For simplicity we assumed that the hydrogen bond between the inhibitor and the tubulin residue Asn226 did not deviate significantly from the ideal hydrogen bond geometry. The score function that we used is shown below: Modified LUDI score function=MS×BS×2.93+85×(H-bond#)−NR×24.2−95, Log $K_d$=−Score/100; where NR is the number of rotatable bond; MS is the molecular surface calculated by MS program; BS is the percentage of the surface area in contact with the protein residues; H-bond# is the number of hydrogen bonds; and $K_d$ is the binding constant.

Example 2
Synthesis of COBRA-1 and COBRA-2

The synthesis of the first enantiomerically pure prototype compound targeting this unique binding cavity was accomplished in an efficient two-step procedure using the THF epoxide 8[7] as a template as outlined in Scheme 1. After the first step of epoxide opening in compound 8 by undecylmagnesium bromide, the debenzylation during the second and final step resulted in the formation of compound 8.1 with an overall yield of 82%.

Because the mono-THF head portion attached to a long aliphatic chain resembles the shape of a cobra, we designated compound 8.1 as "COBRA-1".

The benzyl-protected control compound 8.2 was synthesized in one step by using methyl phenyl sulfone as the nucleophile for the epoxide opening of compound 8. The methyl-containing control compound 8.3, lacking a long aliphatic chain, was prepared by catalytic hydrogenation of compound 8, whereas the hydroxymethyl-containing control compound 8.4 was synthesized by first treating the previously reported mono-THF compound 7[7] with potassium carbonate in methanol followed by hydrogenation.

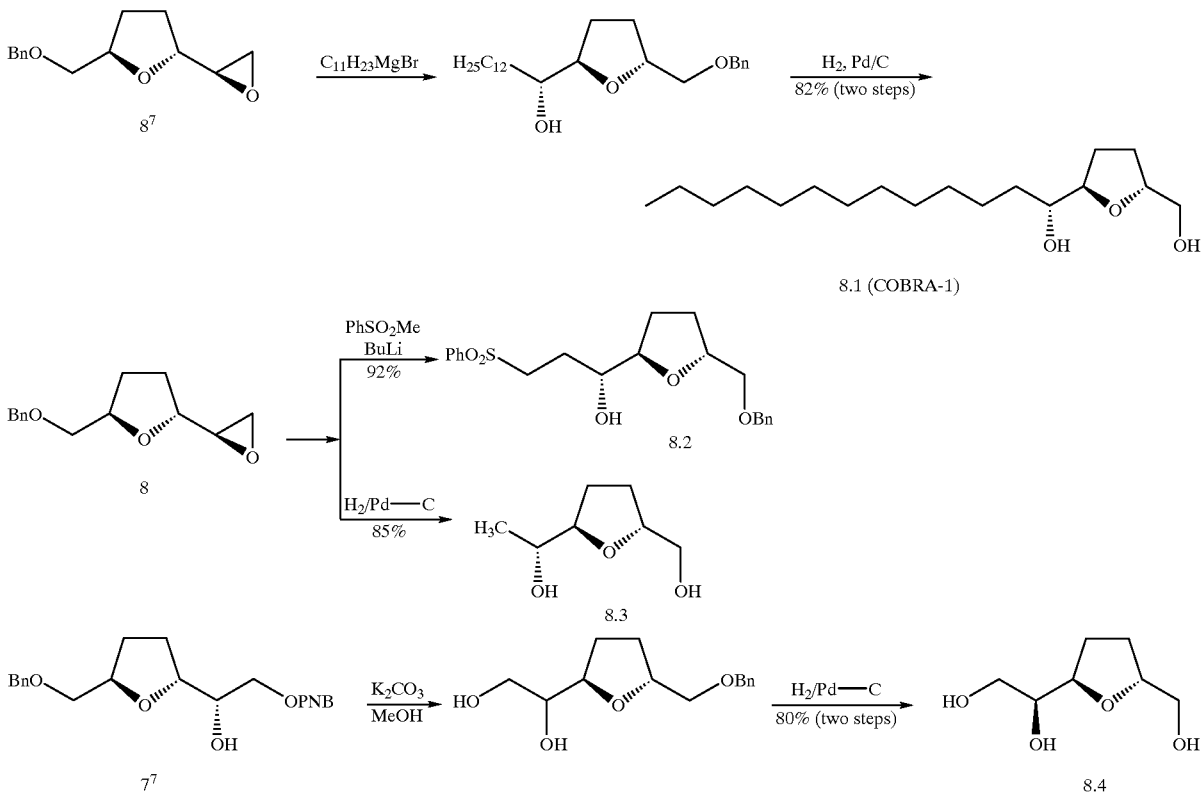

Scheme 1

The precursor compound THF epoxide 8 for the synthesis of COBRA-1 was synthesized from benzyl (R)-(-)-glycidyl ether in 13 steps with an overall yield of 44%. The requisite configurations of the three stereogenic centers in THF epoxide 8 were established by the enantiomerically pure benzyl (R)-(-)-glycidyl ether 1 and Sharpless asymmetric epoxidation. Formation of the THF-ring was accomplished by acid catalyzed epoxide ring opening and 5-exo cyclization reaction[7].

Specific Synthesis and Characterization of Compound COBRA-1

To a suspension of Mg (0.23 g, 10 mmol) in ether (20 mL) at room temperature was added dropwise 1-bromoundecane in 2 hours. The mixture was refluxed for 30 minutes. After being cooled down to room temperature, the reaction mixture (15 mL) was transferred to the flask containing CuBr (0.11 g, 0.76 mmol) in THF (10 mL) at 0° C., followed by the addition of epoxide 8 (0.30 g, 1.28 mmol) in THF (3 mL). The reaction was stirred at 0° C. for 1 hour and it was then quenched with $NH_4Cl$ (25 mL). The reaction mixture was partitioned between EtOAc (100 mL) and water (100 mL). The organic layer was washed with brine, dried over $MgSO_4$ and concentrated. Flash column chromatography (hexane/EtOAc=8:2) afforded the benzyl-protected precursor (0.440 g, 85% yield) as a colorless liquid. $^1$H NMR (300 MHz, $CDCl_3$) δ7.32 (m, 5H), 4.56 (m, 2H), 4.15 (m, 1H), 3.82 (m, 1H), 3.45 (m, 2H), 3.36 (m, 1H), 2.44 (BS, 1H), 2.02–1.92 (m, 2H), 1.65 (m, 2H), 1.51–1.24 (m, 22H), 0.86 (t, J=7.0 Hz, 3H).

To the solution of the benzyl-protected precursor compound (0.40 g, in ethylacetate (30 mL)), a catalytic amount of Pd/C was added. The reaction mixture was stirred under a $H_2$ atmosphere for 24 hours and then filtered through the celite pad. The organic layer was concentrated and flash chromatography ($CHCl_3$/MeOH=95:5) was done to afford: COBRA-1

(0.28 g, 97%) yield as pale solid. $^1$H NMR (300 MHz, $CDCl_3$) δ4.08 (m, 1H), 3.81 (m, 1H), 3.57 (m, 1H), 3.49 (m, 1H), 3.39 (m, 1H), 2.39 (d, J=6.0 Hz, 1H), 2.03–1.93 (m, 3H), 1.68 (m, 2H), 1.49–1.23 (m, 22H), 0.86 (t, J=6.5 Hz, 3H); $^{13}$C NMR (75 MHz, $CDCl_3$) δ82.90, 79.63, 74.15, 64.76, 33.41, 31.94, 29.68, 29.38, 28.54, 27.82, 25.62, 22.71, 14.16; IR (neat) 3406, 2924, 2854, 1466, 1068, 758 $cm^{-1}$; $[\alpha]_D^{22}$ 49.0 (c 2.45, $CHCl_3$).

Synthesis and Characterization of Compound 8.2

To a solution of methyl phenyl sulfone (0.47 g, 3.0 mmol) in THF (10 mL) at −78° C. was added n-BuLi (3.0 mmol, 1.2 mL of 2.5 M solution in hexane). After being stirred at −78° C. for 30 minutes, $BF_3$:$OEt_2$ (3.0 mmol) was added, followed by the addition of the solution of epoxide 8 (0.234 g, 1.0 mmol) in THF (5.0 mL). The resulting mixture was stirred at −78° C. for 2 hours. After being warmed up to room temperature, the reaction was quenched with saturated $NH_4Cl$ solution. The reaction mixture was partitioned between EtOAc and water. The organic layer was washed with brine, dried over $MgSO_4$ and concentrated. Flash column chromatography (hexane/EtOAc=8:2) afforded: Compound 8.2

(0.36 g, 94%). $^1$H NMR (300 MHz, $CDCl_3$) δ7.89 (m, 2H), 7.66–7.52 (m, 3H), 7.31 (m, 5H), 4.54 (m, 2H), 4.16–4.06 (m, 1H), 3.78 (m, 1H), 3.46–3.32 (m, 4H), 3.18 (m, 1H), 2.46 (bs, 1H), 2.01–1.57 (m, 6H); $^{13}$C NMR (75 MHz, $CDCl_3$) δ139.1, 138.0, 133.6, 129.2, 128.3, 127.9, 127.6, 82.1, 78.4, 73.3, 72.6, 72.0, 53.0, 28.7, 28.0, 26.5; IR (neat) 3444, 2924, 2868, 1446, 1306, 1149, 1086, 917, 743, 698 cm$^{-1}$; $[\alpha]_D^{22}$ 189.1 (c 3.26, CHCl$_3$).

Synthesis and Characterization of Compound 8.3

The solution of THF-epoxide 8 in ethylacetate (0.12 g, 0.512 mmol) was stirred under H$_2$ atmosphere for 24 hours in the presence of catalytic amount of Pd/C (5 mg). The reaction mixture was filtered through a celite pad and the organic layer was concentrated. Flash column chromatography (CHCl$_3$/MeOH=95:5) afforded:

Compound 8.3

(0.073 g, 98%) as a colorless liquid. $^1$H NMR (300 MHz, CDCl$_3$) δ4.07 (m, 1H), 3.79–3.46 (m, 4H), 2.04 (m, 2H), 1.76–1.54 (m, 2H), 1.11 (d, J=6.5 Hz, 3H); $^{13}$C NMR (75 MHz, CDCl$_3$) δ84.3, 79.8, 70.6, 64.7, 28.5, 27.8, 18.7; IR (neat) 3383, 1026 cm$^{-1}$; $[\alpha]_D^{22}$ −99.2 (c 1.32, CHCl$_3$).

Synthesis and Characterization of Compound 8.4

To the solution of compound 7[7] (0.15 g, 0.37 mmol) in MeOH (10 mL) at 0° C. was added NaOMe (0.1 g, 1.86 mmol) and the resulting mixture was stirred at room temperature for 1 hour. The methanol was removed and the residual was partitioned between EtOAc and water. The organic layer was washed with brine, dried over MgSO$_4$, filtered and concentrated to afford the diol as shown in Scheme 1. The crude diol was used in next step without further purification. $^1$H NMR (300 MHz, CDCl$_3$) δ7.31 (m, 5H), 4.59 (d, J=12.5 Hz, 1H), 4.55 (d, J=12.5 Hz, 1H), 4.19 (m, 1H), 3.96 (m, 1H), 3.78 (m, 1H), 3.70–3.56 (m, 2H), 3.43 (m, 2H1), 2.44 (bs, 1H), 2.20 (bs, 1H), 2.04–1.59 (m,4H).

The solution of diol in ethylacetate (7 ML) was stirred under H$_2$ atmosphere for 24 hours in the presence of catalytic amount of Pd/C (5 mg). The mixture was filtered through a celite pad and the organic layer was concentrated. Flash column chromatography (CHCl$_3$/MeOH=9:1) afforded:

Compound 8.4

(0.049 g, 83%) as a colorless liquid. $^1$H NMR (300 MHz, CDCl$_3$) δ4.1 (m, 1H), 3.96 (m, 1H), 3.66 (m, 4H), 3.49–3.38 (m, 2H), 3.22 (bs, 1H), 3.02 (bs, 1H), 1.96 (m, 2H), 1.85 (m, 1H), 1.66 (m, 1H). $^{13}$C NMR (75 MHz, CDCl$_3$) δ80.20, 79.82, 73.25, 64.90, 63.60, 27.50, 27.43.

COBRA-2

Synthesis of the second enantiomerically pure prototype compound (COBRA-2) targeting the unique binding cavity of tubulin was accomplished with a 90% yield in an efficient single-step procedure by opening the epoxide of the previously reported THF epoxide 1[8] using allylmagnesium bromide (Scheme 2).

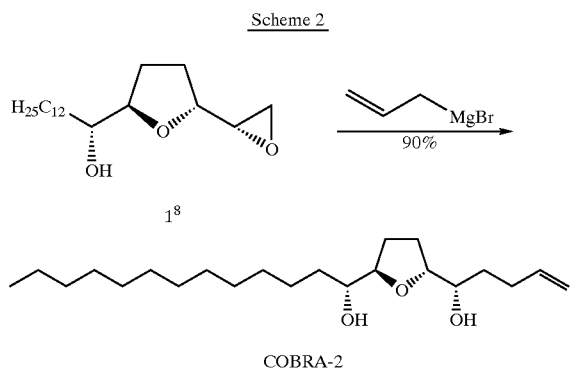

Scheme 2

Starting from the commercially available tridecanal, stereoselective synthesis of THF epoxide 1, an epoxy tetrahydrofuran (THF) containing a versatile synthetic precursor for COBRA-2, was accomplished in 11 steps with an overall yield of 24%, as previously reported in detail[8]. The requisite configurations of the stereogenic centers in the epoxy tetrahydrofuran containing compound 1 were established by Sharpless asymmetric epoxidation and Sharpless asymmetric dihydroxylation. Formation of the THF-ring unit was accomplished by acid catalyzed epoxide ring opening and 5-exo cyclization reaction.

Specific Synthesis and Characterization of COBRA-2

A solution of 1 (3.78 g, 12.09 mmol) in anhydrous THF (25 mL) was added dropwise to the mixture of allyl magnesium chloride (18.13 mL of 2M solution in THF) and CuBr (0.60 g, 4.23 mmol) in anhydrous THF (150 mL) at 0° C. The reaction mixture was stirred for 1 hour and quenched with saturated ammonium chloride. The mixture was partitioned between ethyl acetate (300 mL) and water (300 mL). The organic phase was washed with brine (75 mL), dried over anhydrous MgSO$_4$, filtered and concentrated. Flash column chromatography furnished compound.

COBRA-2

As a white solid (3.85 g, 90%). $[\alpha]_D^{23}$ +24.3° (c 0.20, CDCl$_3$); IR (neat) 3421.2, 2921.7, 2850.3, 1635.4, 1066.5, 669.2 cm$^{-1}$; $^1$H-NMR (CDCl$_3$) δ5.83–5.69 (m, 1H), 5.01–4.89 (m, 2H), 3.83–3.72 (m, 3H), 3.33–3.31 (m, 1H), 2.44 (s, 1H), 2.25–1.76 (m, 6H), 1.65–1.18 (m, 24H), 0.88–0.78, (t, 3H, J=6.5 Hz); $^{13}$C-NMR (CDCl$_3$) δ138.21, 114.85, 83.39, 82.17, 74.36, 70.87, 33.14, 31.92, 31.63, 30.21, 29.65, 29.35, 28.63, 25.56, 25.34, 22.69, 14.13; HRMS m/e (M+1) calcd 355.3134, found 355.3212.

Example 3

Interactions of COBRA-1 and COBRA-2 With the Novel COBRA Binding Pocket on Tubulin Both COBRA-1 and COBRA-2 were docked into the putative COBRA binding pocket near the taxol binding site on beta tubulin and the same region on alpha tubulin using the Affinity module within the INSIGHTII program desdcribed above. The binding region has approximate dimensions of 6 Å×22 Å×7 Å (FIG. 1). The long aliphatic chain of COBRA-1 and COBRA-2 interact with the leucine (or isoleucine) residues 209, 212, 217, 219, 234, 231, 230, 268 and 276. Additionally, the THF rings of both compounds can form favorable interactions with tubulin via hydrogen bonds with residue Asn226 on α tubulin. Finally, the binding constants for COBRA-1 and COBRA-2 were calculated based on their docked positions using a modified LUDI score function.

The results of our molecular modeling and docking studies indicated that both molecules would fit much better into the binding cavity on α tubulin than the corresponding region on β tubulin. The reason for this selectivity may involve an enclosure on the target binding cavity which is provided in part by an 8-amino acid insertion loop in alpha tubulin (residues 361–368), which is not present in beta tubulin.

Both compounds have a total molecular surface area of 350 Å$^2$ (defined by Connolly[9], approximately 256 Å$^2$ of which is in contact with the binding pocket on α tubulin based on our calculations. The estimated Ki values for COBRA-1 were 70 μM for α tubulin and 2.6 mM for β tubulin. The estimated Ki values for COBRA-2 were 75 μM for α tubulin and 2.9 mM for β tubulin.

FIG. 1A shows a ribbon representation of the α tubulin structure and a space-filling model of the compound COBRA-1 which was docked into the taxol binding mirror site on α tubulin, prepared by Molscript and Raster 3D[10–12] based on the electron crystallographic structure of tubulin[6]. The compound COBRA-1 forms extensive interactions with the leucine-rich region located in and extending beyond the taxol binding mirror site on α tubulin. Most of the residues in the binding site are identical for α and β tubulin. The binding site on α tubulin has an eight amino acid insertion (residues 361–368) which provides additional hydrophobic contact and constitute the major difference between the taxol binding site on β tubulin. The figure was prepared using Raster3D and Molscript programs[10, 12].

Figure 1B:
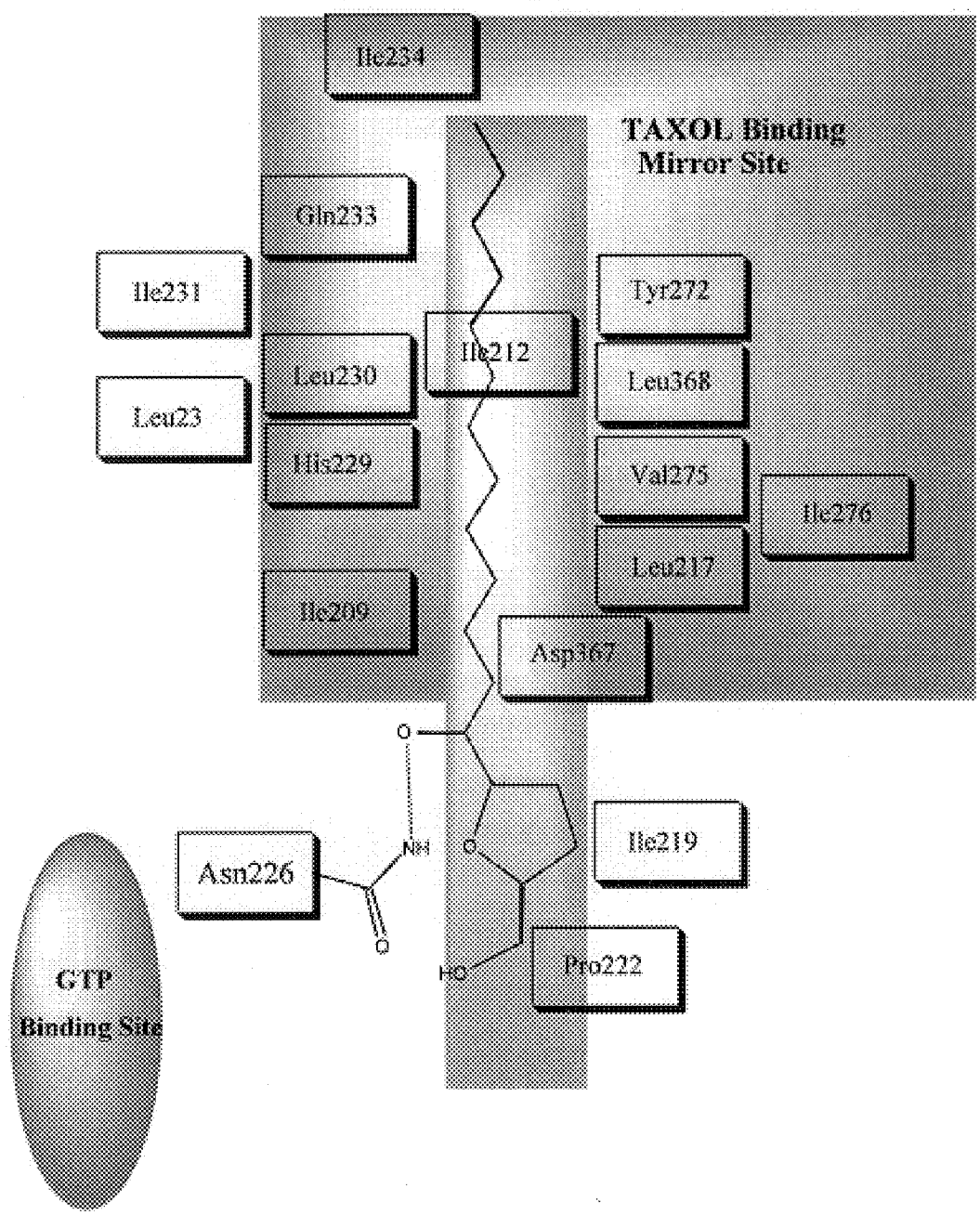
FIG. 1B is a schematic drawing of COBRA-1 interacting with protein residues in the target binding pocket of α tubulin.

FIG. 1B is a schematic drawing showing COBRA-1 interacting with protein residues in the target binding pocket of α tubulin. In contrast to COBRA-1 and COBRA-2, the control compounds 8.2 and 8.4, which do not contain the long aliphatic chain, were not predicted to bind effectively to tubulin due to a considerable loss of hydrophobic interactions.

Example 4
Effects of COBRA Compounds on Tubulin Polymerization

The occupation of the binding pocket by COBRA-1 or COBRA-2 was predicted to interfere with the formation of the α/β tubulin dimer and induce tubulin depolymerization. These predictions were experimentally confirmed in tubulin turbidity assays[13]. Both compounds caused partial depolymerization of tubulin and inhibited its polymerization in the presence of GTP.

Turbidity Measurements

Bovine brain tubulin (Sigma, St. Louis, Mo.) was used in standard turbidity assays to test the effects of compounds COBRA-1 and COBRA-2 as well as control compounds on GTP-induced tubulin polymerization. Compounds (in 1% DMSO) were added to tubulin (1 mg/ml, 0.1M MES, 1 mM EGTA, 0.5mM $MgCl_2$, 0.1 mM EDTA, 2.5M glycerol, 1 μg/ml leupeptin, 1 μg/ml aprotinin, pH 6.5) followed by stimulation of polymerization with 1 mM GTP at 2 minutes and 1 mM taxol at 30 minutes. Optical density was measured using a Becton Dickinson UV spectrophotometer (350 nm) using a thermostated cuvette holder to keep the reaction at 37° C. Readings obtained from the spectro-photometer were standardized by subtracting the background absorbance of the compound in water from the sample reading following drug addition.

Figure 2A:
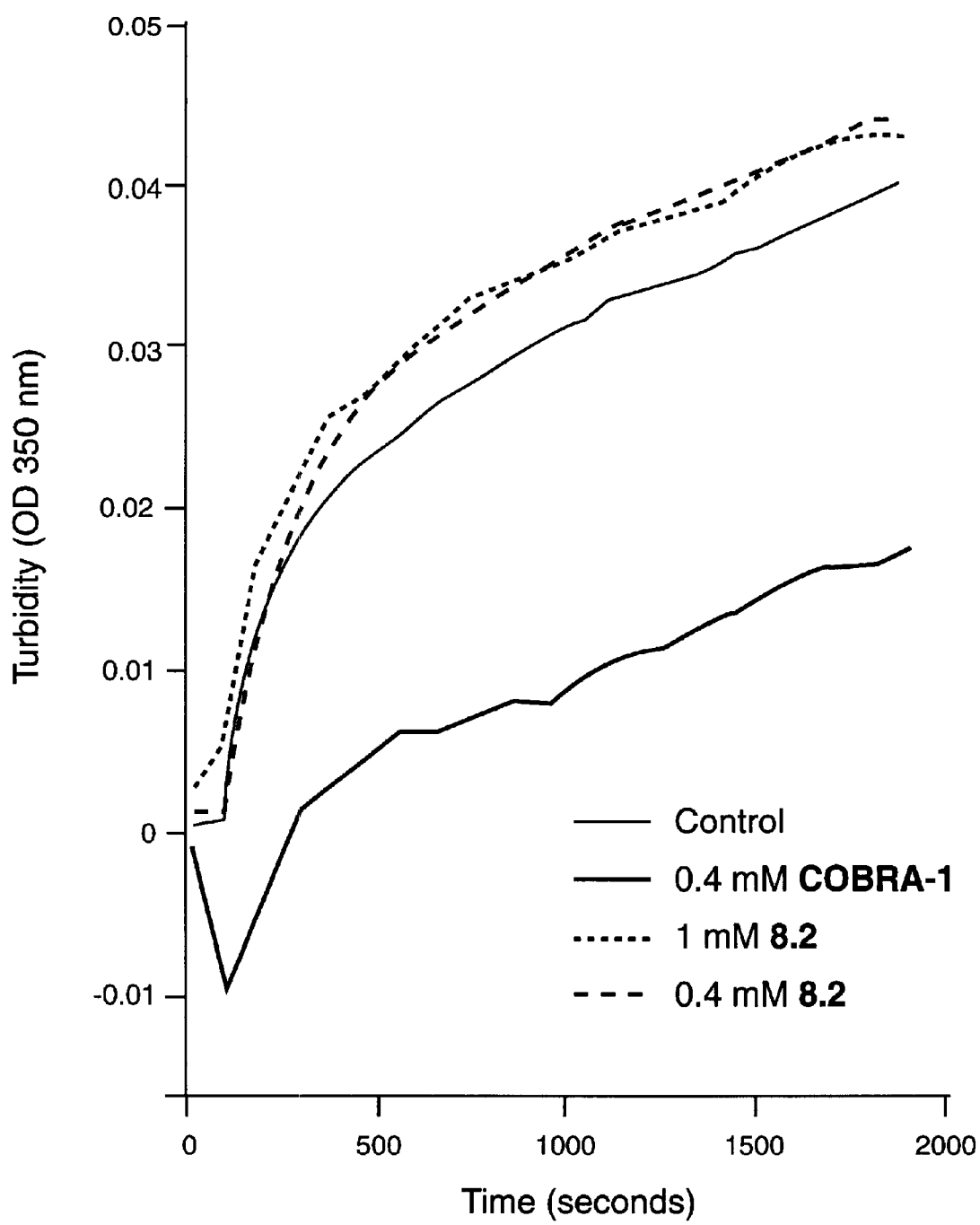
FIGS. 2A–2C are graphs showing the effect of COBRA-1 and COBRA-2 on GTP-dependent tubulin polymerization.
Figure 2B:
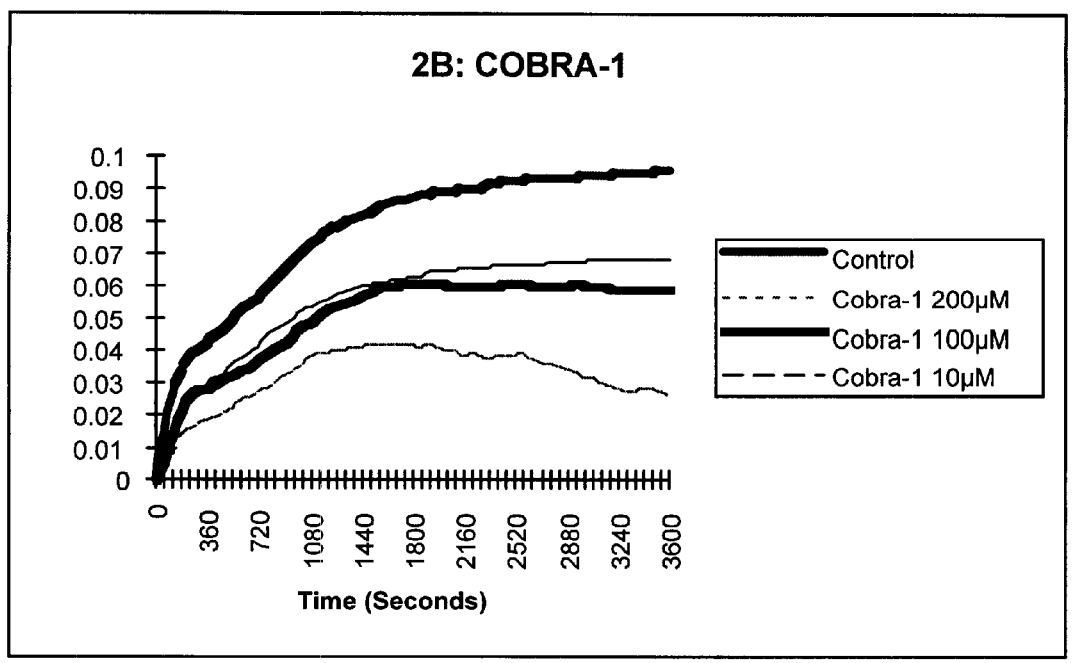
Figure 2C:
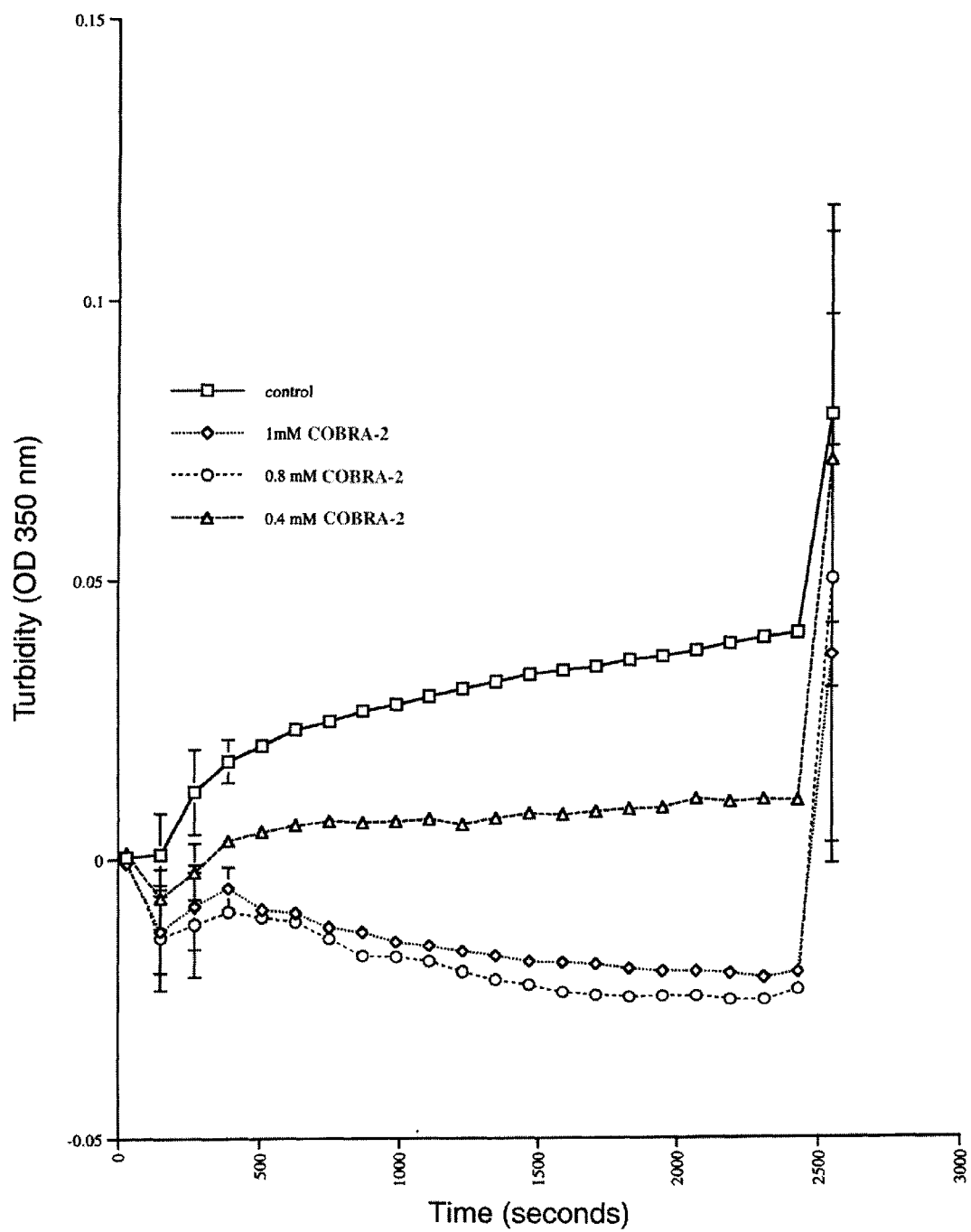

The data are shown in FIGS. 2A–2B, and demonstrate that both COBRA-1 and COBRA-2 caused partial depolymerization of tubulin and inhibited its polymerization in the presence of GTP. FIG. 2A compares the turbidity induced by control, 0.4 mM COBRA-1, and 0.4 mM and 1 mM compound 8.2. FIG. 2B shows the turbidity response of COBRA-1 at 10, 100, and 200 μM doses compared to a control. FIG. 2C shows the turbidity of COBRA-2 at 0.4, 0.8, and 1 mM doses compared to a control.

Example 5
Anti-proliferative Effects of COBRA-1 in the Zebrafish Embryo Model System The embryonic development of the zebrafish (ZF) (*Danio rerio*) has been thoroughly studied and staged. In the ZF meroblastic eggs, rapid cell divisions occur after the ooplasmic segregation on the animal pole of the egg cell, resulting within the first 3 hours of development in the generation of a multicellular blastula comprised of several thousands of cells. The first series of cell divisions of the initial cleavage stage are approximately synchronous only 15 minutes apart and each set of the dividing blastomeres is characterized by a distinct pattern of cellular localization. This remarkable proliferation rate of undifferentiated eukaryotic vertebrate cells makes the ZF embryo an attractive experimental model for screening organic compound libraries for novel anti-mitotic or cytotoxic agents[14–16].

ZF eggs were removed from their chorions by mild digestion in 1% Trypsin-EDTA (Sigma) for 10 minutes at 28.5° C. (Standard temperature—ST), washed three times in "egg water"[15–16] and twice in "embryonic medium" (EM)[15–16]. The dechorionated two-cell stage cleaving eggs/embryos were transferred to the 24-well plastic cell culture plates (Costar, City, State) filled with EM or Hank's Balanced Salt Saline (HBSS, Gibco, City, State). Dechorionated embryos (10–12 per well) were exposed to the drugs at a constant ST for 0.5–24 hours. The final volume of the media in each well was 500 μL. All reference as well as test compounds were used at concentrations ranging from 10 μM to 4 mM. The title compounds were dissolved in DMSO and then diluted serially with the incubation medium. The final concentration of DMSO in the wells was 1.2% (with the exception of the etoposide treatment where it was 3%). The sham-treated control embryos were incubated in EM or HBSS in the presence of 1.2% (or 3%) DMSO.

Observations of cell division and development of the ZF embryos were carried out using a SMZ-10A stereo microscope (Nicon, City, State), once every 30 minutes within the first 3 hours of incubation and at 6, 12 and 24 hours, as well. The drug effect was considered to be revealed when all embryos from one well were affected in a characteristic manner in 3 independent experiments. The stereo microscope was fitted with a specially designed transparent heating tray in order to keep embryos at ST during observations. Pictures of the embryos were taken with a H-III Photomicrographic System (Nicon) using Ektachrome 64× film (Kodak, Rochester, N.Y.).

Figure 3:
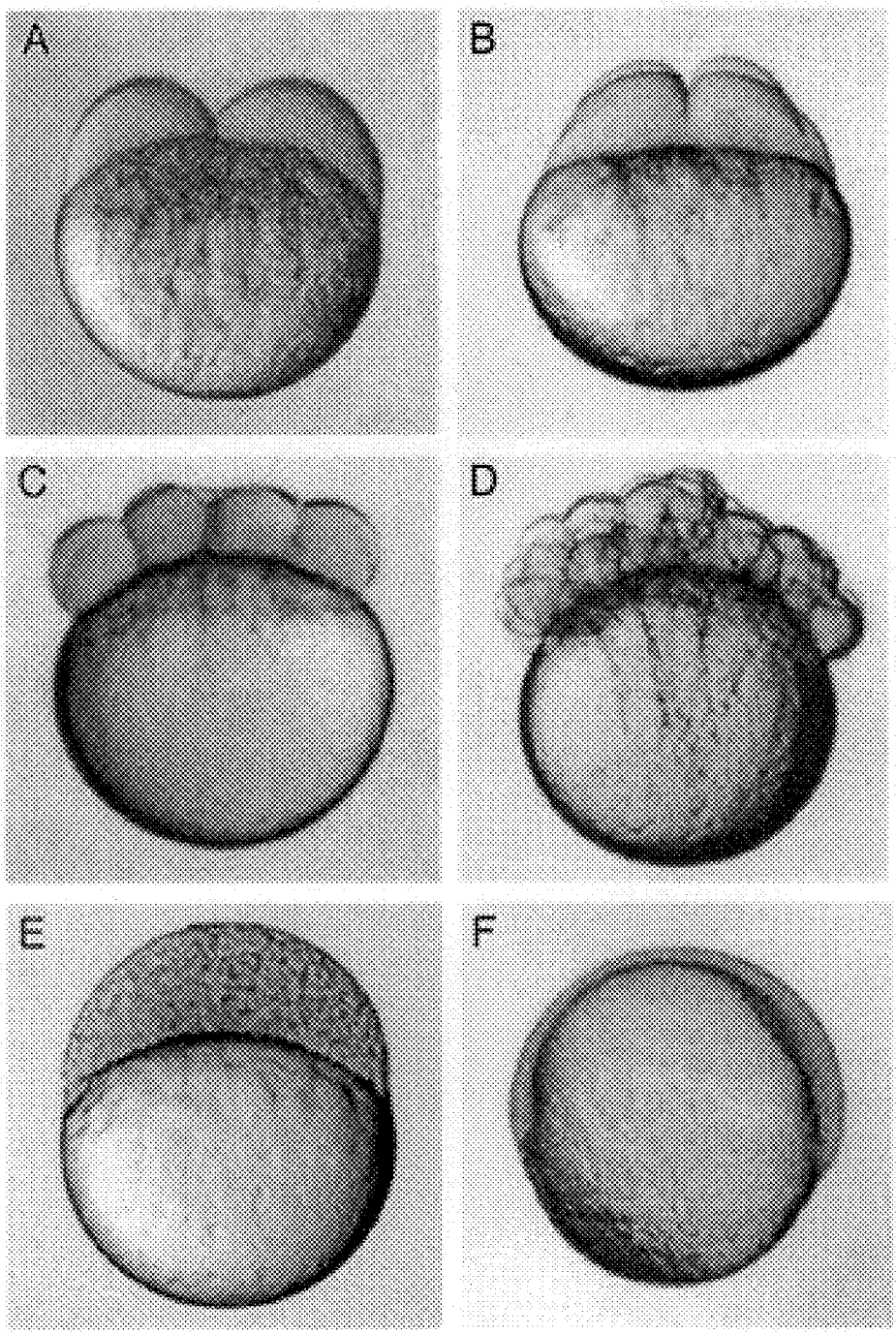
FIGS. 3A–3F are photographs showing normal mitosis in the zebra fish embryo. Untreated or sham-treated two-cell stage ZF embryos at 0, 15, 30 and 75 minutes (FIGS. 3A–D). Within 3.5 hours post fertilization the embryo develops into a high blastula (FIG. 3E) and undergoes gastrulation some 2.5 hours later (FIG. 3F)

Untreated or sham-treated two-cell stage ZF embryos (FIG. 3A) reached 4-cell, 8-cell, and 64-cell stages in 15, 30, and 75 minutes, respectively (FIGS. 3B–D). Within 3.5 hours post fertilization the embryo developed into a high blastula (FIG. 3E) and underwent gastrulation some 2.5 hours later (FIG. 3F).

Incubation of the ZF embryos in the presence of the vinca alkaloid vincristine had a rapid and dramatic result. At concentrations of 100 μM in EM or HBSS, two-cell stage embryos stopped cleaving within 15 minutes, never to form a 4 cell stage embryo. Fifteen minutes later, the membrane between the first 2 blastomeres melted and in the course of reverse development a blastodisk was formed, similar to that of the late one-cell stage. Thus, vincristine treatment of the ZF embryos caused rapid total cell division blockade, cell fusion and developmental arrest. By comparison, the ZF embryos treated with paclitaxel at concentrations of 400 μM in EM showed developmental abnormalities after 90 minutes of exposure. The embryos responded to paclitaxel exposure at first by cell disorientation and dispersal all around the animal hemisphere of the egg instead of their compaction in blastoderm shaping. This was followed by partial and eventually total cell fusion.

In contrast to the tubulin targeting compounds vincristine and taxol, the antimetabolite methotrexate caused morphogenetic alteration and developmental arrest of the ZF embryos at gastrulation. Incubation of the ZF embryos with methotrexate had no visible effect on cell division during the cleavage and blastula stages, and by 4 hours of incubation the cell size and the shape of the blastoderm remained unchanged. However, all of the embryos treated with 1–4 mM of the drug failed to gastrulate. There was no epiboly in these embryos to be seen at 7 hours; instead the dome shape of the blastoderm turned to a cone-like form, usually, with huge wedges of cytoplasm which separated the cell mass from the yolk. None of these embryos developed any further.

Figure 4:
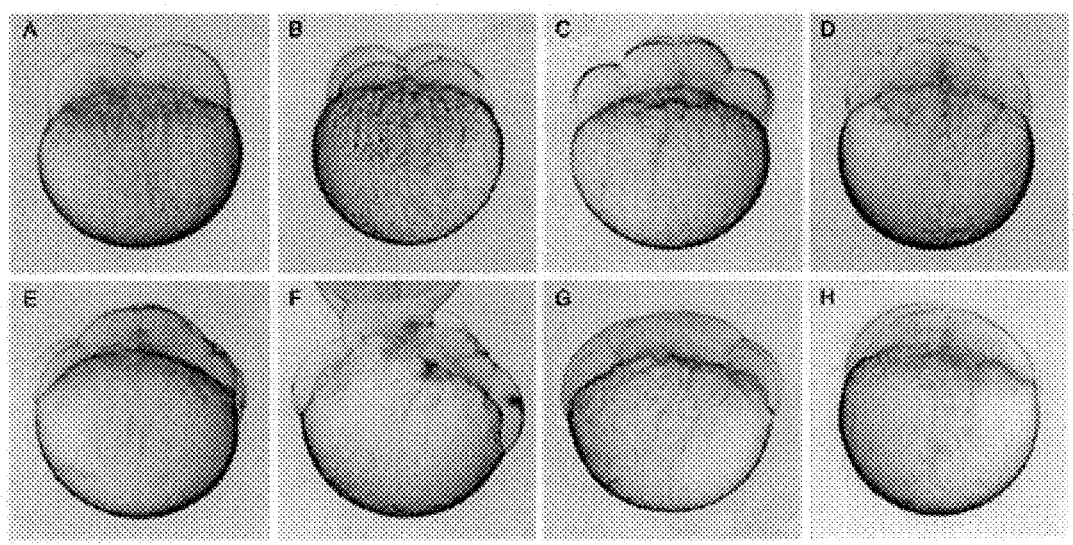
FIGS. 4A–4H are photographs showing anti-proliferative effects of COBRA-1 in the ZF embryo model system. Control embryo at 5, 20, 35, and 60 minutes of incubation (FIGS. 4A–4D); Cobra-1 treated embryo (200 μM; 30 minutes)(FIG. 4E); (400 μM;30 minutes)(FIG. 4F); (200 μM;60 minutes)(FIG. 4G); and (400 μM; 60 minutes)(FIG. 4H).

When the two-cell stage ZF embryos were treated with COBRA-1 at 200 and 400 μM concentrations, they developed normally for 30 minutes, up to the 8-cell stage, and then showed an immediate arrest of proliferation followed by cell fusion (FIGS. 4A–H). Pictures of the control embryo were taken at the two-cell stage after five minutes (FIG. 4A), at the four-cell stage after 20 minutes (FIG. 4B), at the eight-cell stage after 35 minutes (FIG. 4C), and at the sixteen-cell stage after 60 minutes of incubation in EM with 1% DMSO (FIG. 4D). Embryo treated with 200 μM of COBRA-1 for 30 minutes show the start of cell fusion (FIG. 4E); embryo treated with 400 μM of COBRA-1 for 30 minutes show deterioration of cell division and start of cell fusion (FIG. 4F). The adjacent cells from two embryos fuse together. Embryo treated with 200 μM of COBRA-1 for 60 minutes show cell division blockade, total fusion and developmental arrest (FIG. 4G); and embryo treated with 400 μM of COBRA-1 for 60 minutes show cell division blockade, total fusion and developmental arrest (FIG. 4H).

Example 6
Effects of COBRA-1 and COBRA-2 on the Mitotic Index of Human Cancer Cells Confocal microscopy was used as previously described[17] to determine the mitotic indices of BT-20 human breast cancer cells and U373 human brain tumor cells 24 hours after treatment with COBRA-1 or COBRA-2. Immunofluorescence was used to examine the morphologic features of human cancer cells treated with COBRA-1 or COBRA-2.

Cells were incubated at 37° C. for the indicated time periods with the title compounds. At the end of the incubation, cells were washed twice with PBS and fixed in 2% paraformaldehyde. The cells were permeabilized and non-specific binding sites were blocked with 2.5% BSA in PBS containing 0.1% Triton X-100 for 30 minutes. Tubulin expression was examined by immunofluorescence using a monoclonal antibody against α-tubulin (Sigma Chemical Co, St. Louis, Mo.) at a dilution of 1:1000 and an anti-mouse IgG conjugated to FITC. Cells were washed in PBS and counterstained with toto-3 (Molecular Probes Inc., Eugene, Oreg.) for 10 minutes at a dilution of 1:1000. Cells were washed again with PBS and the coverslips were mounted with Vectashield (Vector Labs, Burlingame, Calif.) and viewed with a confocal microscope (Bio-Rad MRC 1024) mounted in a Nikon Labhophot upright microscope. Digital images were saved on a Jaz disk and processed with Adobe Photoshop software (Adobe Systems, Mountain View, Calif.).

In some experiments, COBRA-1 treated brain tumor cells were labeled with the membrane dye DiA and imaged using multiphoton microscopy. The individual tumor cells were imaged 1 hour before adding 100 μM COBRA-1. The total imaging period was 3 hours.

Figure 5:
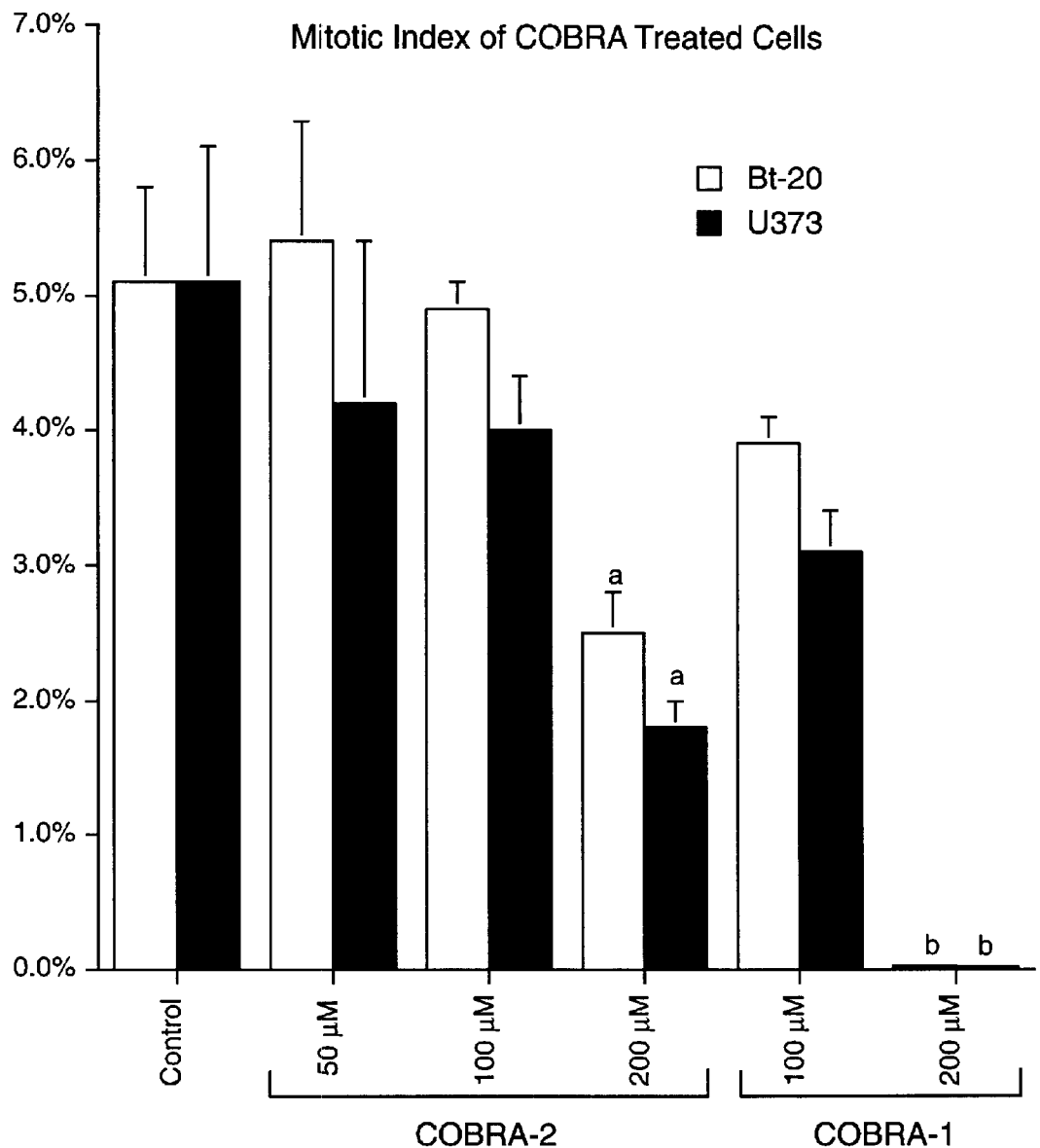
FIG. 5 is a graph showing inhibition of cellular mitotic index in COBRA treated breast cancer and brain tumor cells.

As shown in FIG. 5, both compounds significantly reduced the mitotic indices of these cancer cell lines. Thus, COBRA compounds are anti-mitotic agents consistent with their tubulin depolymerizing activity.

Example 7
Anti-Cancer Activity of COBRA-1 as Measured by MTT Assays

The antiproliferative activity of COBR+A-1 and the control mono-THF containing compounds 8.2, 8.3, and 8.4 was examined against a panel of 5 different human tumor cell lines using standard MTT (3-[4,5-dimethylthiazol-2-yl]-2, 5-diphenyl tetrazolium bromide) assays[18] (Boehringer Mannheim Corp., Indianapolis, Ind.).

Briefly, exponentially growing brain tumor cells were seeded into a 96-well plate at a density of $2.5 \times 10^4$ cells/well and incubated for 36 hours at 37° C. prior to drug exposure. On the day of treatment, culture medium was carefully aspirated from the wells and replaced with fresh medium containing the test or control compounds at concentrations ranging from 0.1 to 250 μM. Triplicate wells were used for each treatment. The cells were incubated with the various compounds for 24–36 hours at 37° C. in a humidified 5% $CO_2$ atmosphere. To each well, 10 μl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbence of each well was measured in a microplate reader (Labsystems) at 540 nm and a reference wavelength of 690 nm. To translate the $OD_{540}$ values into the number of live cells in each well, the $OD_{540}$ values were compared to those on standard $OD_{540}$-versus-cell number curves generated for each cell line. The percent survival was calculated using the formula: % survival=Live cell number[test]×100/Live cell number [control].

$IC_{50}$ values were calculated by non-linear regression analysis using an Graphpad Prism software version 2.0 (Graphpad Software, Inc., San Diego, Calif.).

TABLE 1

Anti-Cancer Activity of COBRA-1 Against Human Tumor Cell Lines

| Compounds | MDA-MB-231 | PC-3 | SQ20B | U87 | NALM-6 |
| --- | --- | --- | --- | --- | --- |
| | $IC_{50}$ [MTT] (μM) | | | | |
| COBRA-1 | 77 | 171 | 140 | 107 | 49 |
| 8.2 | >250 | >250 | >250 | >250 | >250 |

TABLE 1-continued

Anti-Cancer Activity of COBRA-1 Against Human Tumor Cell Lines

| Compounds | MDA-MB-231 | PC-3 | SQ20B | U87 | NALM-6 |
|---|---|---|---|---|---|
| | $IC_{50}$ [MTT] ($\mu$M) | | | | |
| 8.3 | >250 | >250 | >250 | >250 | >250 |
| 8.4 | >250 | >250 | >250 | >250 | >250 |

Cell Lines

The following human cancer cell lines were used in the present study: BT-20, breast cancer; MDA-MB-231, breast cancer; PC3, prostate cancer; U87 and U373, glioblastoma; NALM-6, B-lineage acute lymphoblastic leukemia. These cell lines were obtained from American Type Culture Collection (Manassas, Va.) and maintained as continuous cell lines in Dulbecco's modified Eagles's medium supplemented with 10% fetal bovine serum and antibiotics. The data are shown in Table 1 and FIGS. 6A–6C. All cell lines were inhibited by COBRA-1 in a dose-dependent fashion, but not by compounds 8.2, 8.3, or 8.4.

Example 8
Anti-cancer Activity of COBRA-1 as Measured by Microscopy
Transmission Electron Microscopy The ultrastructural changes in human breast and glioblastoma cancer cells treated with COBRA-1 or COBRA-2 were examined by confocal microscopy and by transmission electron microscopy, using methods previously reported[19].

Figure 7:
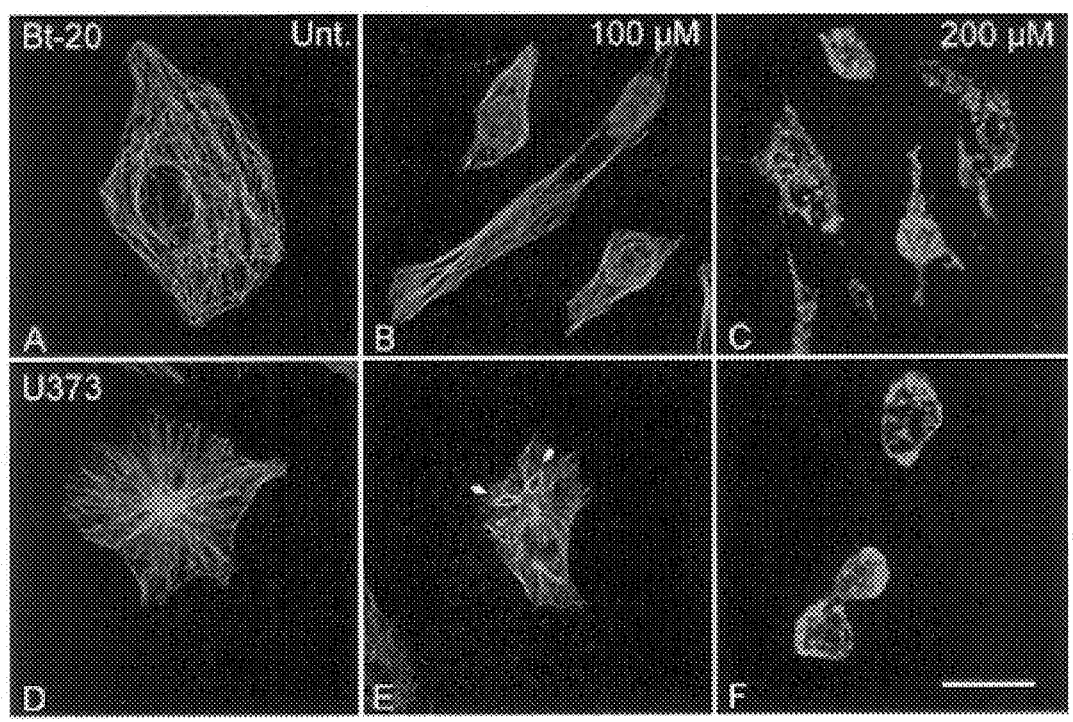
FIG. 7 are photographs demonstrating cytotoxicity of COBRA-1 against human breast cancer cells (FIGS. 7A–7C) and brain tumor cells (FIGS. 7D–7F), as documented by confocal microscopy; Untreated (FIGS. 7A and 7D); 100 μM Cobra-1 (FIGS. 7B and 7E); 200 μM (FIGS. 7C and 7F).

FIGS. 7A–7C document by confocal microscopy the cytotoxicity of COBRA-1 against breast cancer cells. BT-20 breast cancer cells are large adherent cells with a well organized microtubule cytoskeleton (FIG. 7A). When treated for 24 hours with 100 $\mu$M COBRA-1, the cells shrink and the microtubules become less organized (FIG. 7B). Treatment with 200 $\mu$M COBRA-1 results in cell death with nuclear fragmentation and complete loss of microtubule formation (FIG. 7C).

Similar results are observed in U373 brain tumor cells (FIGS. 7D–7F). The addition of 100 $\mu$M COBRA-1 induces abnormal tubulin structures (FIG. 7E, arrows). In the color photographs, the microtubules are shown by green fluorescence, while DNA is blue. The bar indicates size of 20 microns. Treatment with 200 $\mu$M COBRA-1 results in cell death with nuclear fragmentation and complete loss of microtubule formation (FIG. 7F).

Figure 8:
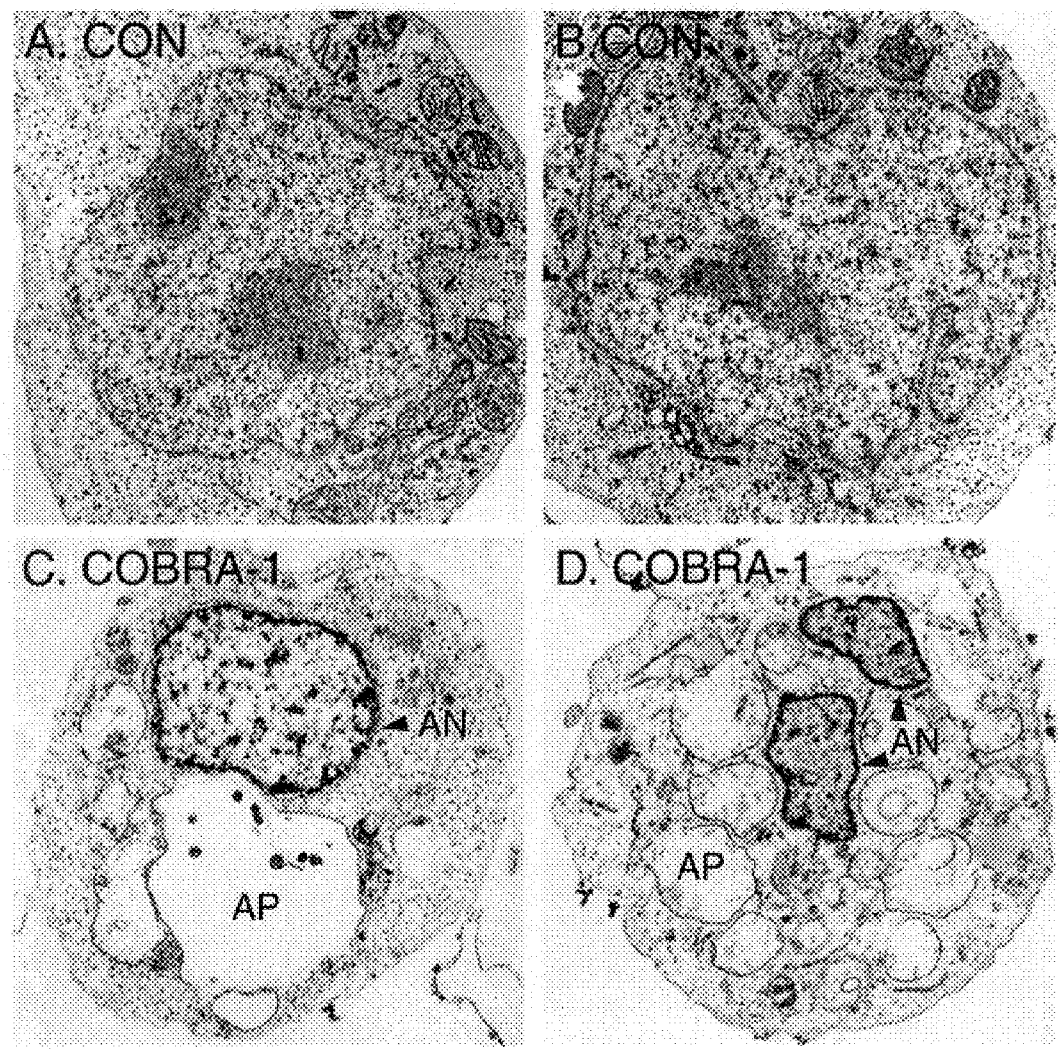
FIGS. 8A–8D are photographs showing cellular effects of COBRA-1 on Nalm-6 leukemia cells by Transmission Electron Microscopy; Controls (FIGS. 8A–8B); Treated cells (FIGS. 8C and 8D).

FIGS. 8A–8D are transmission electron micrographs of Nalm-6 leukemia cells treated with COBRA-1. In contrast to the control cells (FIGS. 8A and 8B), the treated leukemia cells (100 mM) showed nuclear fragmentation, chromatin condensation, and formation of multiple autophagosomes, consistent with apoptosis (FIGS. 8C and 8D).

Using two-photon confocal laser scanning microscopy, the kinetics of COBRA-1 induced apoptosis in tumor cells was shown to be fast with a rapid onset at approximately 1 hour after exposure and total destruction within approximately 24 hours (FIGS. 9A–9F). U373 brain tumor cells were labeled with the membrane dye DiA and imaged using two-photon microscopy.

Figure 9:
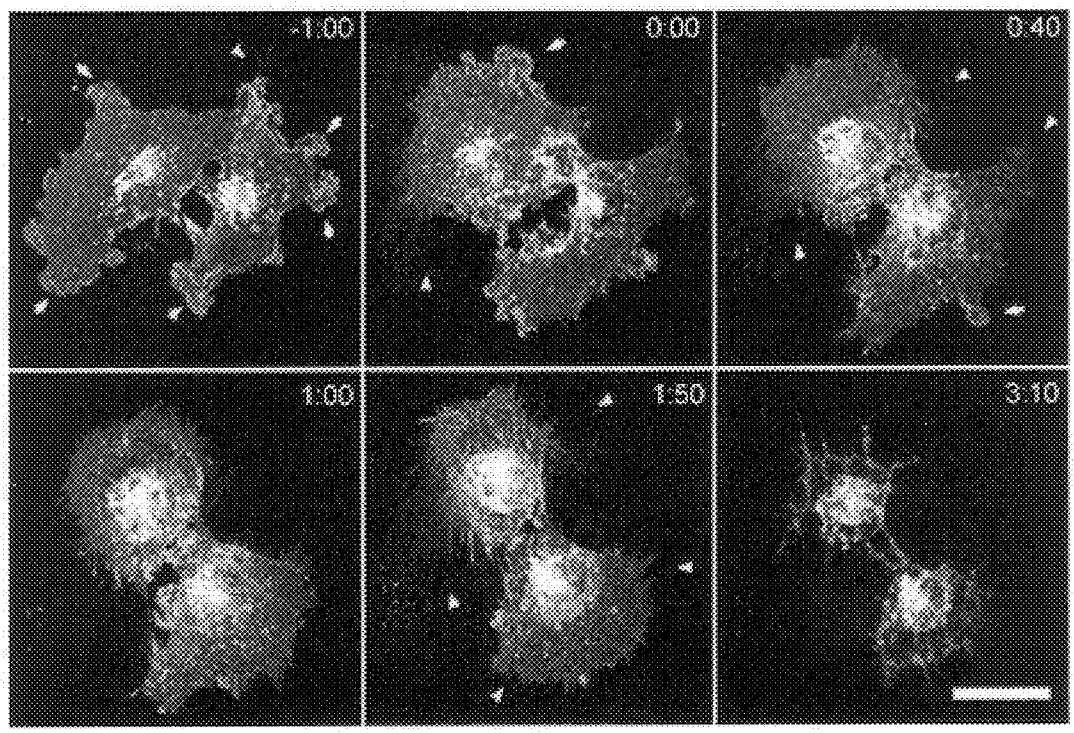
FIGS. 9A–9F are photographs showing cytotoxicity of COBRA-1 against glioblastoma cells as documented by two-photon confocal microscopy; Control (FIG. 9A) and treated cells at time 0 (FIG. 9B), 40 seconds (FIG. 9C), 1 minute (FIG. 9D), 1 minute 50 seconds (FIG. 9E), and 3 minutes 10 seconds (FIG. 9F).

Arrows denote membrane ruffles formed in the direction that the cell is crawling. Arrowheads denote the trailing edge or the edge where the cell is retracting. The cell was imaged 1 hour before adding 100 $\mu$M DDE261 (FIG. 9A). Within 40 minutes of drug addition, only one membrane ruffle is still evident (FIG. 9C), and after 1 hour, only trailing edges are present (FIG. 9D). The cell continued to shrink throughout the 3 hour imaging period (FIGS. 9E and 9F). The white material in the color photographs is the dye, DiA. The Scale Bar denotes 20 microns.

Example 9
Anti-Cancer Activity of COBRA-2

Treatment of tumor cells with COBRA-2 caused destruction of microtubule organization and apoptosis, as documented by confocal laser scanning microscopy.

Figure 10:
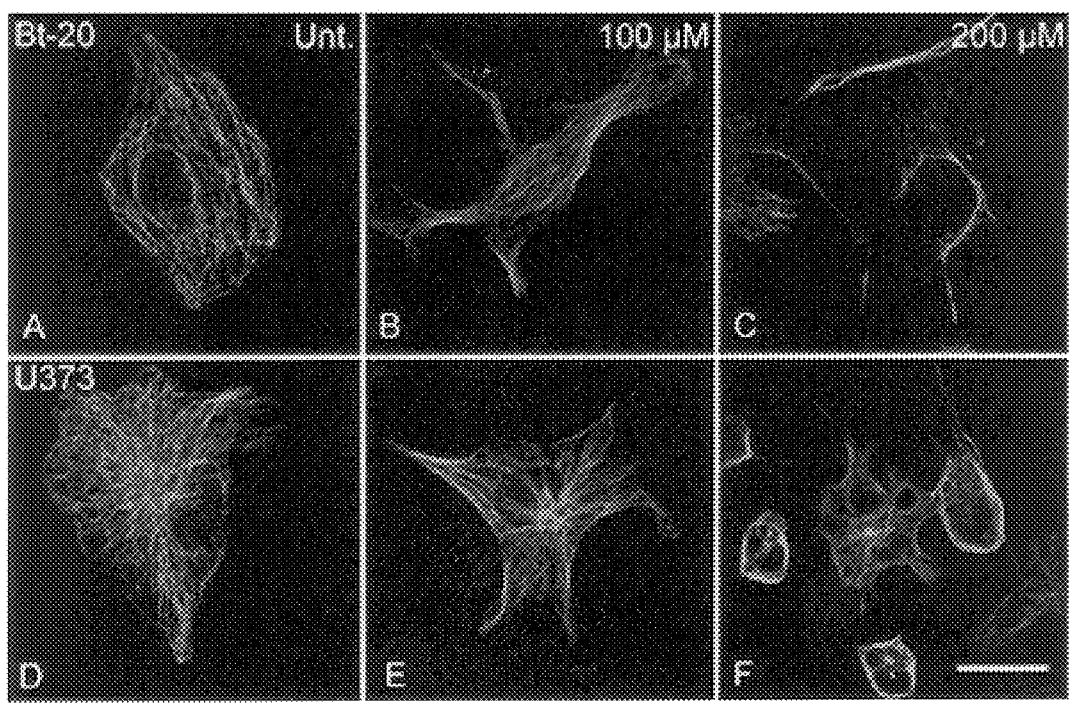
FIGS. 10A–10F are photographs showing cytotoxicity of COBRA-2 against human breast cancer (FIGS. 10A–10C) and brain tumor cells (FIGS. 10D–10F), as documented by confocal microscopy; Controls (FIGS. 10A and 10D); 100 μM (FIGS. 10B and 10E); and 200 μM (FIGS. 10C and 10F).
Figure 11:
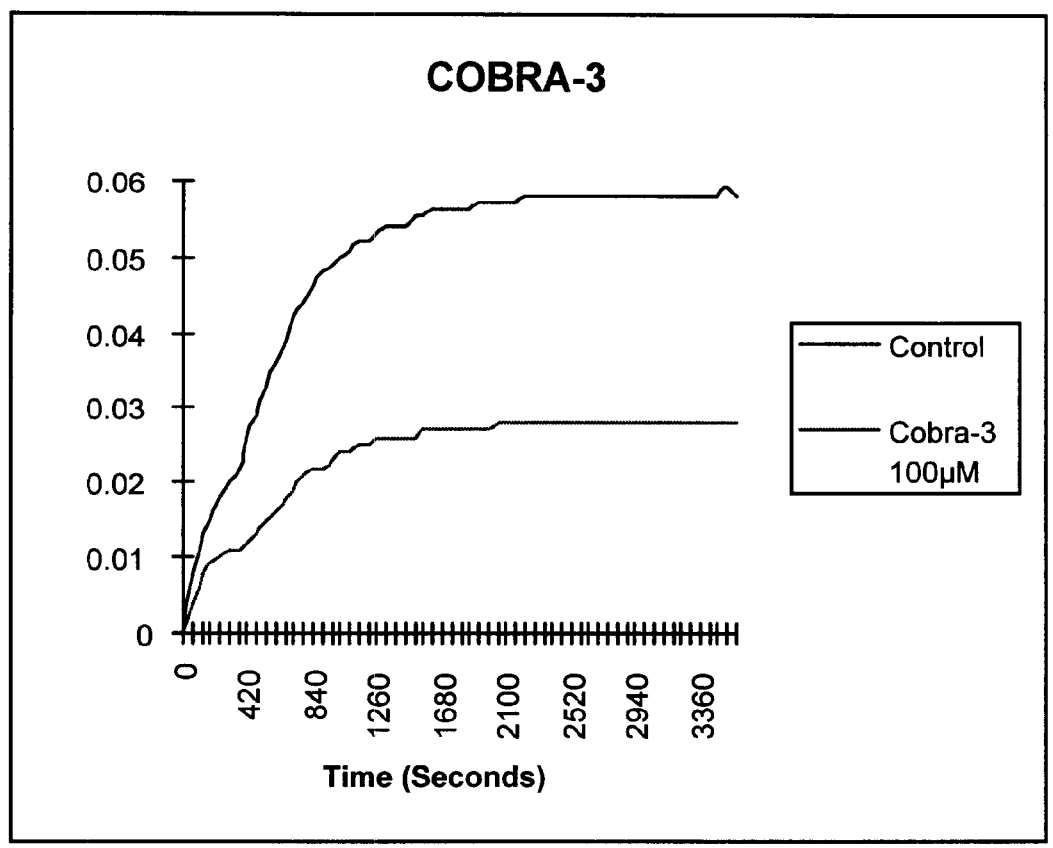
FIG. 11 is a graph showing the effect of COBRA-3 on GTP-dependent tubulin polymerization.
Figure 12:
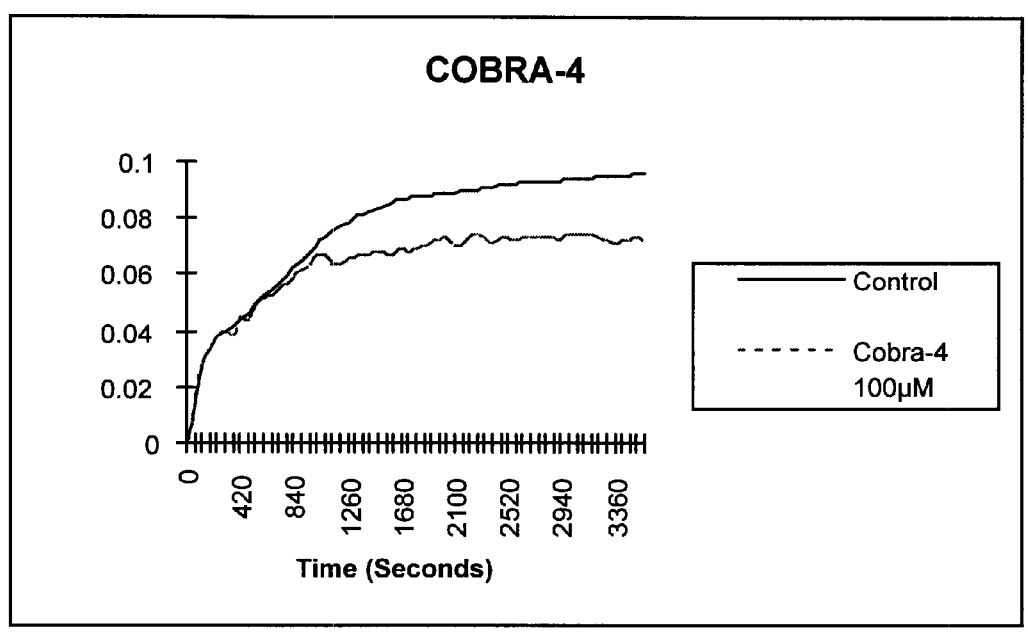
FIG. 12 is a graph showing the effect of COBRA-4 on GTP-dependent tubulin polymerization.
Figure 13:
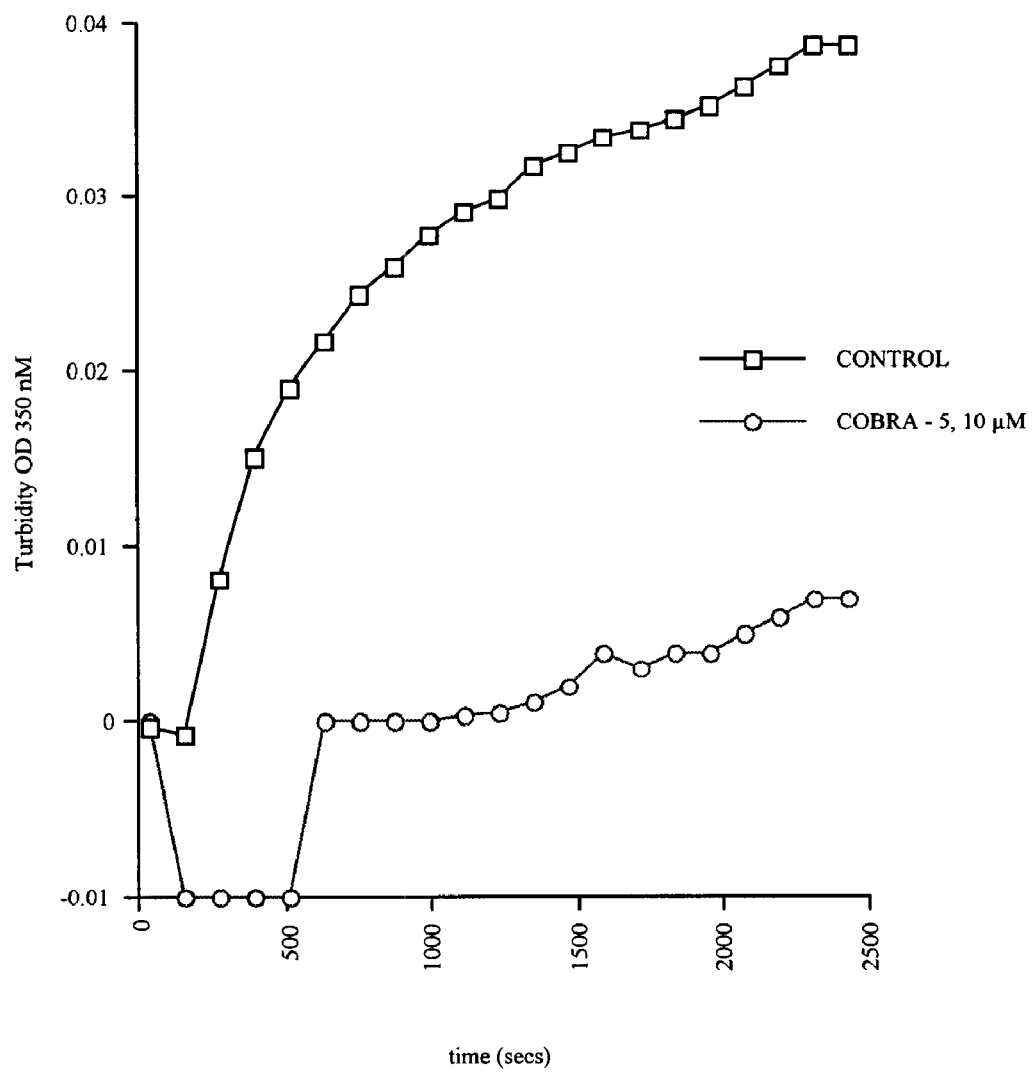
FIG. 13 is a graph showing the effect of COBRA-5 on GTP-dependent tubulin polymerization.
Figure 14:
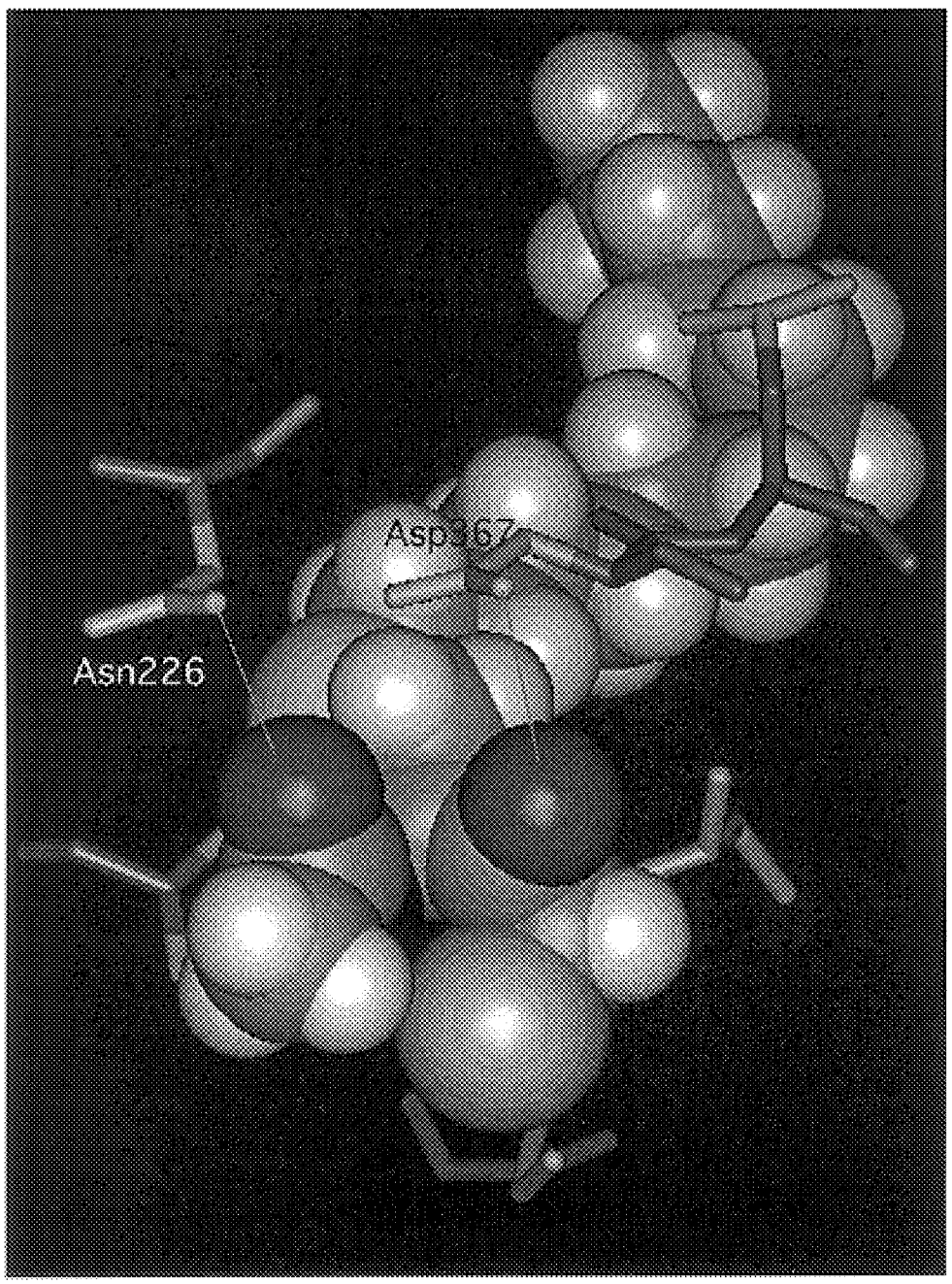
FIG. 14 shows a space-filing model of COBRA-5 docked in the target binding pocket of α tubulin.

BT-20 breast cancer cells (FIG. 10A) and U373 glioblastoma cells (FIG. 10D) are large cells with a well organized microtubule cytoskeleton. When treated for 24 hours with COBRA-2, the cells shrink and the microtubules become less organized (FIGS. 10B and 10E). Treatment with 100–200 $\mu$M COBRA-2 results in cell death with nuclear fragmentation and complete loss of microtubule formation. See FIGS. 10A–10B for results in breast cancer cells, and FIGS. 10E and 10F for results in glioblastoma cells. In the color photographs, green flourecense indicates microtubules, and blue is DNA. The bar denotes a size of 20 microns.

Summary of the Data

In summary, we used a three-dimensional computer model of tubulin constructed based upon its recently resolved electron crystallographic structure for rational design of a novel class of synthetic anti-cancer drugs targeting a previously unrecognized unique narrow binding cavity on the surface of tubulin. This unique binding pocket has elongated dimensions and was predicted to favorably interact with the aliphatic side chains of the lead compounds COBRA-1 and COBRA-2. Our modeling studies also indicated that both compounds are capable of favorable interactions with tubulin via hydrogen bonding with the Asn226 residue.

The anti-cancer activity of COBRA-1 and COBRA-2 was confirmed using MTT assays, confocal laser microscopy, and transmission electron microscopy. Both compounds caused destruction of microtubule organization, mitochondrial damage, and apoptosis. Using two-photon confocal laser scanning microscopy, the kinetics of apoptosis in tumor cells was shown to be fast with a rapid onset at approximately 1 hour after exposure and total destruction within approximately 24 hours.

Example 10
Synthesis and Characterization of COBRA-3

Modeling studies of COBRA-1 and COBRA-2 docked into the COBRA target binding site of tubulin revealed additional sterically available space which could be successfully exploited for the design of potentially more effective members of this novel class of anti-cancer agents. The narrow binding cavity provides close contacts with the long chain of the compound and reduces the feasibility of adding "branches" on the long aliphatic chain of COBRA compounds as a derivatizing strategy for making new inhibitors.

The THF binding region extending from the hydrophobic cavity is relatively exposed and thus is more forgiving in accommodating different substituents on the THF ring at the opposite side of the long chain (FIG. 2). This binding region is also more hydrophilic and is compatible with the hydroxyl group and the oxygen atom of the THF-ring. These observed geometric features of the binding site may provide the structural basis for the future development of more potent COBRA compounds targeting this binding region.

To test the latitude of the structure at the opposite end of the molecule from the long chain (head region), three new COBRA compounds were synthesized according to the schemes shown below: COBRA-3, COBRA-4, and COBRA-5. Each of these compounds was then tested for tubulin depolymerization activity, using the tubidity assay described in the Examples above.

Synthesis of COBRA-3

Compound COBRA-3 was synthesized in one step from the commercially available 5-(hydroxymethyl)furfural and dodecylmagnesium chloride (Scheme 3). In this novel compound, the chiral THF moiety of COBRA-1 is replaced with the achiral furan moiety.

Scheme 3

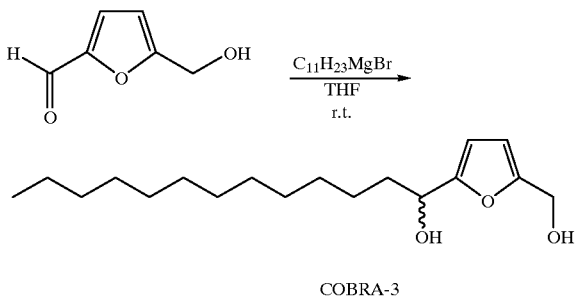

COBRA-3

Dodecylmagnesium chloride (25 mL of 1M solution in ether) was added to the solution of 5-(hydroxymethyl) furfural (1.26 g, 10.0 mmol) in anhydrous ether (15 mL) at 0° C. The reaction mixture was stirred at room temperature for 3 hours and then quenched with saturated ammonium chloride. The mixture was partitioned between ether (120 mL) and water (30 mL). The organic phase was washed with brine, dried over anhydrous $MgSO_4$, filtered and concentrated. Flash column chromatography furnished product compound:

COBRA-3

As a white solid (2.58 g, 87%). mp 56–57° C.; $^1H$ NMR (300 MHz, $CDCl_3$) δ6.14 (d, J=3.5 Hz, 1H), 6.09 (d, J=3.5 Hz, 1H), 4.55 (t, J=7.0 Hz, 1H), 4.46 (s, 2H), 3.22 (bs, 1H), 3.06 (bs, 1H), 1.77 (m, 2H), 1.41–1.20 (m, 17H), 0.85 (t, J=6.5 Hz, 3H); $^{13}C$ NMR ($CDCl_3$) δ156.65, 153.10, 108.13, 106.33, 67.56, 57.12, 35.28, 31.96, 29.73, 29.71, 29.67, 29.62, 29.48, 29.41, 25.70, 22.75, 14.19; IR (neat) 3195, 2922, 2845, 1468, 1014 $cm^{-1}$.

Synthesis of COBRA-4

COBRA-4 was synthesized (Scheme 4) by the asymmetric dihydroxylation of the known compound $9^8$, which is a synthetic intermediate for the synthesis of the THF-epoxide 1 (Scheme 2), to afford COBRA-4.

Scheme 4

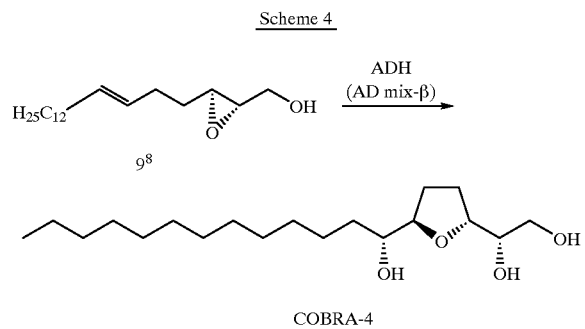

A solution of AD mix-β (600 mg) in t-BuOH (5 mL) and $H_2O$ (5 mL) was stirred at ambient temperature for 10 minutes to produce two clear phases. Methanesulfonamide (60.1 mg, 0.63 mmol) was added and the mixture was cooled to 0° C. Compound 9 (100 mg, 0.34 mmol) in t-BuOH (3 mL) and $H_2O$ (3 mL) was added at once and the reaction was stirred for 20 hours at 0° C. Sodium sulfite (600 mg) was added and the mixture was allowed to warm to room temperature and stirred for 1 hour. The mixture was then partitioned between ethyl acetate and water. The organic phase was washed with brine, dried over $MgSO_4$, filtered and concentrated to give crude COBRA-4. The crude product was purified by column chromatography to afford the final product:

COBRA-4

(84 mg; 75%). mp 106–108° C.; $^1H$ NMR (300 MHz, $CDCl_3$) δ3.93 (m, 1H), 3.84–3.59 (m, 4H), 3.38 (m, 1H), 2.37 (bs, 1H), 2.29 (bs, 1H), 2.09 (bs, 1H), 2.04–1.80 (m, 2H), 1.71–1.47 (m, 2H), 1.41–1.16 (m, 22H), 0.86 (t, J=6.5, 3H); $^{13}C$ NMR ($CDCl_3$) δ83.06, 79.99, 74.12, 72.91, 63.77, 33.35, 31.94, 29.68, 29.38, 28.37, 27.70, 25.60, 22.72, 14.17; IR (neat) 3361, 2917, 2850, 1127 $cm^{-1}$; LRMS (CI, $NH_3$) m/e 348.3 ($M+NH_4$), 331.3 (M+1), 313.3 ($M-H_2O$); HRMS (CI, $NH_3$) m/e (M+1) calcd 355.3134, found 355.3212; ($M+NH_4$) calcd 348.xxx, found 348.3112.

Synthesis of COBRA-5

COBRA-5, having the structure shown below in Scheme 5, is a chloromethyl ketone compound with a 12C S-alkyl side chain.

Scheme 5

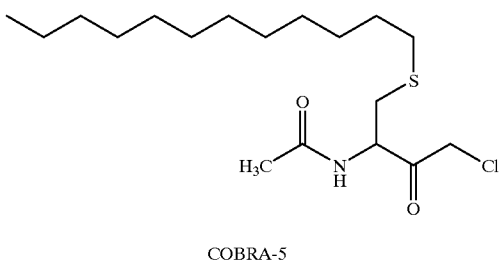

COBRA-5

To synthesize this compound, S-dodecyl-bromide (1.57 g, 1.49 mL, 5.5 mmol) was added to N-Ac-Cys-OH (0.82 g, 5 mmol) in 4 M ammonia in methanol (35 mL) at 0° C. The reaction was stirred at 0° C. for 3 hours, then at room temperature for 1 hour. The solvent was removed under reduced pressure and the residue partitioned between 1-butanol and water. The butanol layer was dried ($MgSO_4$) and the solvent removed under reduced pressure. The residue was redissolved in methanol and washed with hexane. The methanol was then removed under reduced pressure to give N-Ac-S-dodecyl-Cys-OH (a).

The N-Ac-S-dodecyl-Cys-OH (a) (1.84 g, 5 mmol) produced in the previous step, was dissolved in dry THF (30 mL) and cooled to −15° C. 4-methyl morpholine (0.51 g, 0.55 mL, 5 mmol) and iso-butyl chloroformate (0.68 g, 0.65 mL, 5 mmol) were added to the solution. The mixture was stirred at −15° C. for 5 minutes before being filtered by gravity into a solution of diazomethane in ethanolic ether (11 mmol, 30 mL) cooled in an ice bath. The resulting solution was stirred in ice for 3 hours. Excess diazomethane was purged with nitrogen gas and the reaction mixture was washed with 5% sodium bicarbonate solution and water, dried over $MgSO_4$, and then the solvent was removed under reduced pressure. The product was purified by chromatography on silica gel (10–50% ethyl acetate in hexane) to give N-Ac-S-dodecyl-Cys diazomethyl ketone(b).

A solution of HCl in ethyl acetate (1 M, 2 mL, 2 mmol) was added to a solution of the previously synthesized N-Ac-S-dodecyl-Cys diazomethyl ketone (b) (1.57 g, 1 mmol) in ethyl acetate (10 mL) cooled in an ice bath. The reaction mixture was stirred at 0° C. for 5 to 10 minutes until the starting material was consumed by TLC. The solvent was then removed under reduced pressure and the residue purified by chromatography on silica gel (1:3 ethyl acetate:hexane) to give the final product: N-Ac-S-dodecyl-Cys Chloromethyl Ketone (COBRA-5)

Pale yellow solid. Yield 100%, 0.18 g. m.p. 73–74° C. $^1H$ NMR ($CDCl_3$) δ0.88 (t, J=6.7 Hz, 3H), 1.26 (m, 18H), 1.57 (m, 2H), 2.06 (s, 3H), 2.54 (t, J=7.3 Hz, 2H), 2.94 (ABX, J=6.0, 6.3, 13.9 Hz, 2H), 4.35 (m, 2H), 4.91 (m, 1H), 6.31 (br, 1H); $^{13}C$ NMR ($CDCl_3$) δ195.2, 165.3, 50.8, 42.7, 29.6, 28.4, 28.2, 27.3, 25.1, 25.0, 24.9, 24.83, 24.8, 24.7, 24.5, 24.1, 18.3, 18.1, 9.5; IR (KBr) 3302, 2924, 2854, 1738,1660, 1537, 1456, 1377, 1261, 1165, 1095, 1040 $cm^{-1}$; MS (MALDI-TOF), 364.9 (M+1), 328.9 (M−Cl).

Effect of COBRA Compounds on Tubulin Polymerization

Each of these compounds was assayed for effects on GTP-dependent tubulin polymerization, using the methods described above. Each compound, COBRA-3, COBRA-4, and COBRA-5 caused partial depolymerization of tubulin and completely inhibited its polymerization in the presence of GTP, as shown in FIGS. 11–14. COBRA-5 was found to have an $IC_9$, value of 10 μM, and exhibited very potent anti-cancer activity against human cell lines.

Example 11
Modeling Study of COBRA-5 Binding to Tubulin

COBRA-5 was docked into the putative COBRA binding pocket of tubulin using the Affinity module within the INSIGHTII program, described above. In the color photograph, carbon atoms of the compound are colored in green, hydrogen atoms in white, oxygen atoms in red, sulfur in yellow, and chlorine in grey-green. The tubulin residues interacting with COBRA-5 are shown as cylindrical sticks with sidechains shown in pink and the main chain in blue.

The binding region for the long aliphatic chain of COBRA-5 is identical to that for COBRA-1, COBRA-2, COBRA-3, and COBRA-4. The head group (chloromethyl ketone) of COBRA-5 can form two hydrogen bonds with residues Asn226 and Asp367, as shown by the thin pink lines in FIG. 14. These interactions cannot be formed by the other COBRA compounds studied. The binding constant for COBRA-5 was calculated based on its docked position with tubulin using a modified LUDI score function.

The results of our molecular modeling and docking studies indicated that COBRA-5 would fit much better in the binding cavity of α tubulin relative to the corresponding region on β tubulin. Furthermore, the estimated $K_i$ value for COBRA-5 was 18 μM for binding with α tubulin, which is an improvement over other COBRA molecules due to the favorable interactions between the head group of COBRA-5 and the hydrophilic residues in the target binding site of α tubulin.

Figure 15:
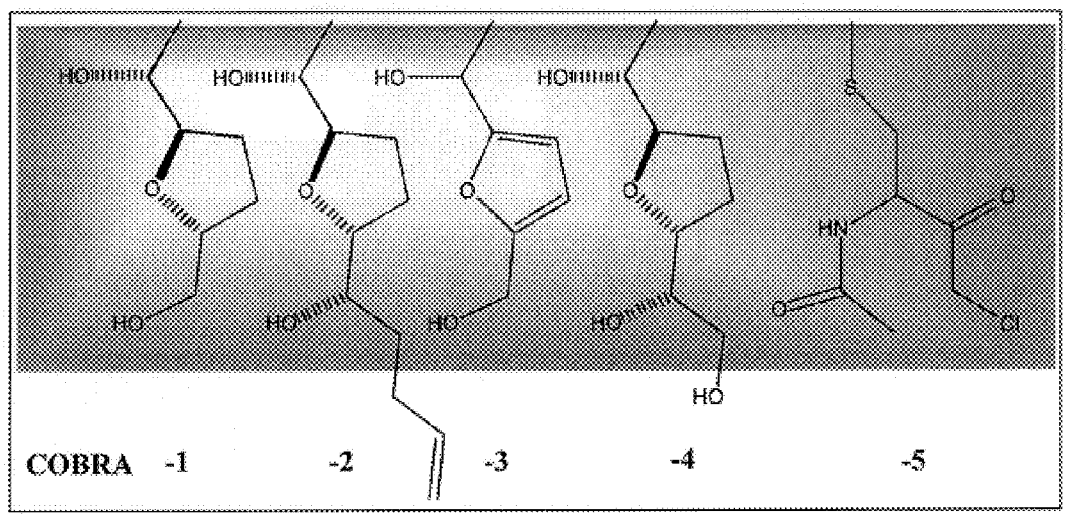
FIG. 15 shows a comparison of the head groups of the compounds COBRA-1 to COBRA-5.

A comparison of the head groups of COBRA-1, -2, -3, -4, and -5 is shown in FIG. 15. COBRA-5, with its two additional groups capable of forming hydrogen bonds with tubulin residues Asn226 and Asp367, exhibited the highest tubulin affinity score among the five compounds, as well as very potent anti-cancer activity. Accordingly, modifications of the head region of COBRA compounds to include hydrogen binding groups for favorable interaction with the binding pocket residues enhances the binding of the molecule to tubulin, provides enchanced anti-tubulin activity (FIG. 13) and thereby potent anti-cancer activity.

All publications, patents, and patent documents described herein are incorporated by reference as if fully set forth. The invention described herein may be modified to include alternative embodiments. All such obvious alternatives are within the spirit and scope of the invention, as claimed below.

We claim:

1. A compound of the formula

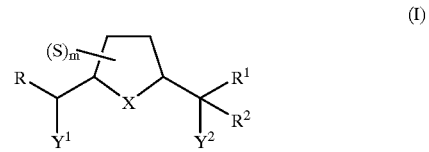

(I)

wherein
    X is S and forms a saturated or unsaturated heterocyclic ring;
    R is a saturated or unsaturated ($C_7$–$C_{15}$) hydrocarbon chain;
    $R^1$ and $R^2$ are independently H, ($C_1$–$C_6$)alkyl, ($C_1$–$C_6$) alkenyl, $C_1$–$C_6$)alkynyl, ($C_3$–$C_7$)cycloalkyl, aryl, or heteroaryl;
    $Y^1$ and $Y^2$ are OH;
    m is 0 to 6;
    each S is independently OH, SH, $CO_2H$, halogen, CN, acyl, thioacyl, ester, thioester, alkoxy, aryloxy, alkylthio, arylthio, alkyl, alkenyl, alkynyl, $(C_3-C_7)$cycloalkyl, aryl, heteroaryl, $C(=O)NR^aR^b$, or $NR^aR^b$; taken together, two of S can form a ring or any two adjacent carbons can form a double bond;

where $R^a$ and $R^b$ are each independently hydrogen, acyl, alkyl, $(C_3-C_7)$cycloalkyl, aryl, or heteroaryl; or $R^a$ and $R^b$ together with the nitrogen to which they are attached form a ring selected from the group consisting of pyrrolidino, piperidino, morpholino, and thiomorpholino; and wherein R, $R^1$, $R^2$, $R^a$, and $R^b$ are independently unsubstituted or substituted with OH, SH, $CO_2H$, halogen, CN, acyl, thioacyl, ester, thioester, $(C_1-C_6)$alkoxy, $(C_1-C_6)$aryloxy, $(C_1-C_6)$alkylthio, $(C_1-C_6)$arylthio, $(C_1-C_6)$alkyl, $(C_1-C_6)$alkenyl, $(C_1-C_6)$alkynyl, $(C_3-C_7)$cycloalkyl, $(C_6-C_{10})$aryl, or $(C_6-C_{10})$heteroaryl.

2. The compound of claim 1, wherein R is a saturated $(C_7-C_{15})$ hydrocarbon.

3. The compound of claim 1, wherein $R^1$ is hydrogen and $R^2$ is H, $CH_2OH$, or $CH_2CH_2CH=CH_2$.

4. The compound of claim 1, wherein two adjacent S form a double bond.

5. A composition comprising the compound of claim 1 and a pharmaceutically acceptable carrier.

6. A method for inhibiting the polymerization or inducing depolymerization of tubulin comprising administering to tubulin a compound of claim 1.

7. A method for inhibiting proliferation of cells comprising contacting said cells with a compound of claim 1.

8. A method for inhibiting the proliferation of tumor cells, comprising administering to said tumor cells an inhibitory amount of the compound of claim 1.

9. A method for treating cancer in a patient, comprising administering to said patient an effective inhibitory dose of a compound of claim 1.

10. A method for treating a cellular proliferation disorder, comprising administering to a patient a compound of claim 1.

* * * * *